(12) United States Patent
Ling et al.

(10) Patent No.: US 10,988,724 B2
(45) Date of Patent: Apr. 27, 2021

(54) THREE-DIMENSIONAL BIOREACTOR FOR CELL EXPANSION AND RELATED APPLICATIONS

(71) Applicant: Southwest Research Institute, San Antonio, TX (US)

(72) Inventors: Jian Ling, Spring Branch, TX (US); Jeffrey N. Harris, San Antonio, TX (US); Michael J. Rubal, Lytle, TX (US)

(73) Assignee: Southwest Research Institute, San Antonio, TX (US)

( * ) Notice: Subject to any disclaimer, the term of this patent is extended or adjusted under 35 U.S.C. 154(b) by 121 days.

(21) Appl. No.: 15/585,812

(22) Filed: May 3, 2017

(65) Prior Publication Data
US 2017/0321178 A1    Nov. 9, 2017

Related U.S. Application Data

(60) Provisional application No. 62/332,177, filed on May 5, 2016.

(51) Int. Cl.
*C12M 1/12* (2006.01)
*C12M 1/00* (2006.01)

(52) U.S. Cl.
CPC ............ *C12M 25/14* (2013.01); *C12M 23/02* (2013.01)

(58) Field of Classification Search
CPC ......... C12M 25/14; C12M 25/16; B01J 19/32
See application file for complete search history.

(56) References Cited

U.S. PATENT DOCUMENTS

| | | | |
|---|---|---|---|
| 4,247,434 A | 1/1981 | Vanderhoff et al. |
| 5,360,609 A | 11/1994 | Wellinghoff |
| 5,443,950 A | 8/1995 | Naughton et al. |
| 5,631,300 A | 5/1997 | Wellinghoff |
| 5,639,295 A | 6/1997 | Wellinghoff et al. |
| 5,650,446 A | 7/1997 | Wellinghoff et al. |
| 5,668,185 A | 9/1997 | Wellinghoff et al. |
| 5,695,814 A | 12/1997 | Wellinghoff et al. |
| 5,705,092 A | 1/1998 | Wellinghoff et al. |
| 5,707,739 A | 1/1998 | Wellinghoff et al. |
| 5,888,528 A | 3/1999 | Wellinghoff et al. |

(Continued)

FOREIGN PATENT DOCUMENTS

| | | |
|---|---|---|
| CA | 2882108 A1 | 3/2014 |
| CA | 3023221 | 11/2019 |

(Continued)

OTHER PUBLICATIONS

English language machine translation of KR20130134080A, pp. 1-12, accessed on Jan. 22, 2019. (Year: 2019).*

(Continued)

*Primary Examiner* — William H. Beisner
(74) *Attorney, Agent, or Firm* — Grossman Tucker Perreault & Pfleger PLLC

(57) ABSTRACT

The present disclosure relates to the design, fabrication, and applications of a three-dimensional (3D) bioreactor for cell expansion and cell secreted substance production. The bioreactor is composed of non-random interconnected voids providing a continuous three-dimensional surface area for cell adherence and growth.

27 Claims, 19 Drawing Sheets
(19 of 19 Drawing Sheet(s) Filed in Color)

(56) References Cited

U.S. PATENT DOCUMENTS

| | | | |
|---|---|---|---|
| 5,914,120 A | 6/1999 | Wellinghoff et al. |
| 5,922,776 A | 7/1999 | Wellinghoff et al. |
| 6,046,243 A | 4/2000 | Wellinghoff et al. |
| 6,277,408 B1 | 8/2001 | Wellinghoff et al. |
| 6,605,304 B1 | 8/2003 | Wellinghoff et al. |
| 7,041,234 B2 | 5/2006 | Wellinghoff et al. |
| 7,094,360 B2 | 8/2006 | Wellinghoff et al. |
| 7,098,359 B2 | 8/2006 | Wellinghoff et al. |
| 7,108,801 B2 | 9/2006 | Wellinghoff et al. |
| 7,147,800 B2 | 12/2006 | Wellinghoff et al. |
| 7,238,831 B2 | 7/2007 | Wellinghoff et al. |
| 7,273,567 B1 | 9/2007 | Wellinghoff et al. |
| 7,678,572 B2 | 3/2010 | Har-Noy |
| 7,956,164 B2 | 6/2011 | Har-Noy |
| 8,007,823 B2 | 8/2011 | Favis et al. |
| 8,012,750 B2 | 9/2011 | Har-Noy |
| 8,399,047 B2 | 3/2013 | Lahann et al. |
| 8,463,418 B2 | 6/2013 | Liu et al. |
| 8,900,610 B2 | 12/2014 | Wellinghoff |
| 8,961,892 B2 * | 2/2015 | Hutter .............. B01F 5/0451 422/129 |
| 9,364,579 B2 | 6/2016 | Wellinghoff |
| 9,410,114 B2 | 8/2016 | Wilson et al. |
| 9,456,893 B2 | 10/2016 | Ling |
| 9,512,393 B2 | 12/2016 | Kasuto et al. |
| 9,593,308 B2 | 3/2017 | Har-Noy |
| 9,663,763 B2 | 5/2017 | Sentman |
| 10,052,372 B2 | 8/2018 | Wang et al. |
| 10,131,876 B2 | 11/2018 | Kaiser et al. |
| 10,179,151 B2 | 1/2019 | Ferber |
| 10,577,585 B2 | 3/2020 | Nguyen et al. |
| 2004/0062809 A1 | 4/2004 | Honiger et al. |
| 2005/0038492 A1 | 2/2005 | Mason et al. |
| 2005/0238683 A1 | 10/2005 | Adhikari et al. |
| 2006/0121005 A1 | 6/2006 | Berenson et al. |
| 2007/0178586 A1 | 8/2007 | Yang et al. |
| 2009/0041825 A1 * | 2/2009 | Kotov .............. C12M 21/08 424/423 |
| 2010/0273667 A1 | 10/2010 | Kotov et al. |
| 2012/0009159 A1 | 1/2012 | Humayun et al. |
| 2012/0208265 A1 | 8/2012 | Partsch et al. |
| 2013/0030548 A1 | 1/2013 | Ling |
| 2013/0084622 A1 | 4/2013 | Ram et al. |
| 2013/0344229 A1 | 12/2013 | Messersmith et al. |
| 2015/0087057 A1 * | 3/2015 | Zink .............. C12N 5/0075 435/366 |
| 2015/0140333 A1 | 5/2015 | Niu |
| 2016/0200891 A1 | 7/2016 | Virgilio et al. |
| 2017/0028042 A1 | 2/2017 | Wang et al. |
| 2017/0051309 A1 | 2/2017 | Lesch et al. |
| 2017/0081638 A1 | 3/2017 | Ma |
| 2018/0016533 A1 | 1/2018 | Tai et al. |
| 2018/0057784 A1 | 3/2018 | Wang et al. |
| 2018/0142200 A1 | 5/2018 | Mason et al. |
| 2019/0002815 A1 | 1/2019 | Wang et al. |
| 2019/0169572 A1 | 6/2019 | Shi et al. |
| 2019/0269768 A1 | 9/2019 | Wang et al. |
| 2019/0276846 A1 | 9/2019 | Lipponen et al. |
| 2019/0292517 A1 | 9/2019 | Cheung et al. |
| 2019/0309250 A1 | 10/2019 | Ling |
| 2020/0071670 A1 | 3/2020 | Shi et al. |
| 2020/0157483 A1 | 5/2020 | Ling et al. |
| 2020/0172864 A1 | 6/2020 | Chiang et al. |
| 2020/0181562 A1 | 6/2020 | McAfee et al. |
| 2020/0190457 A1 | 6/2020 | Veraitch et al. |
| 2020/0208121 A1 | 7/2020 | Hewitt et al. |
| 2020/0248121 A1 | 8/2020 | Ferrie et al. |
| 2020/0248122 A1 | 8/2020 | Ferrie et al. |
| 2020/0248123 A1 | 8/2020 | Ferrie et al. |
| 2020/0248124 A1 | 8/2020 | Ferrie et al. |
| 2020/0255783 A1 | 8/2020 | Ferrie et al. |
| 2020/0255790 A1 | 8/2020 | Veraitch et al. |
| 2020/0255793 A1 | 8/2020 | Oconnor et al. |
| 2020/0283712 A1 | 9/2020 | Wang et al. |

FOREIGN PATENT DOCUMENTS

| | | | |
|---|---|---|---|
| CN | 109689366 | | 4/2019 |
| JP | 2010517590 | | 5/2020 |
| KR | 20130134080 A | * | 12/2013 |
| WO | 2004087797 A1 | | 10/2004 |
| WO | 2008101001 | | 8/2008 |
| WO | 2008140295 A1 | | 11/2008 |
| WO | 2011072393 A1 | | 6/2011 |
| WO | 2012168295 A1 | | 12/2012 |
| WO | 2014037862 A1 | | 3/2014 |
| WO | 2015001321 A1 | | 1/2015 |
| WO | 2015024133 A1 | | 2/2015 |
| WO | 2015086029 A1 | | 6/2015 |
| WO | 2017049066 A1 | | 3/2017 |
| WO | 2017099712 A1 | | 6/2017 |
| WO | 2017192717 A1 | | 11/2017 |
| WO | 2018005521 A1 | | 1/2018 |
| WO | 2018013797 A1 | | 1/2018 |
| WO | 2019194842 | | 10/2019 |
| WO | 2019194842 A1 | | 10/2019 |
| WO | 2020/068840 A1 | | 4/2020 |

OTHER PUBLICATIONS

Kapyla et al. "Direct laser writing and geometrical analysis of scaffolds with design pore . . . ", J. Micromech. Microeng., vol. 22 (2012), pp. 1-13. (Year: 2012).*

Ma et al. "Biodegradable Polymer Scaffolds . . . ", Tissue Engineering, vol. 7 (2001), pp. 23-33 (Year: 2001).*

Ma et al. "Paraffin Spheres . . . ", Wiley Periodicals, (2003), pp. 610-617. (Year: 2003).*

Malinauskas et al. "3D Microporous Scaffolds . . . ", Micromechanics, vol. 5 (2014), pp. 839-858. (Year: 2014).*

Alves da Silva, M., et al, "Chondrogenic Differentiation of Human Bone Marrow Mesenchymal Stem Cells in Chitosan-Based Scaffolds Using a Flow-perfusion Bioreactor"; Journal of Tissue Engineering and Regenerative Medicine; 2011, 5(9), pp. 722-732.

Arifin, M., et al.: "Ultraviolet/Ozone (UV/O3) Treated Polystyrene (PS) Microcarriers for Animal Cell Culture"; Journal of Chemical Technology & Biotechnology 2016, 91(10): pp. 2607-2619.

Boland, E., et al; "In Vitro Cytotoxicity of a Low-shrinkage Polymerizable Liquid Crystal Resin Monomer"; Journal of Biomedical Materials Research Part B, Applied Biomaterials 2006, 79(1): pp. 1-6.

Caicedo-Carvajal, C.E.; 3D Perfusion Bioreactor: The Cumulative Advantages of 3D Scaffold Geometry and Perfusion for Scale-up Processes: 3D Biotek; Technology Center of NJ <<http://www.3DBiotek.com>> accessed Jun. 12, 2019.

Chen, G., et al "Scaffold Design for Tissue Engineering"; Macromolecular Bioscience, 2002, 2, pp. 67-77.

Cheung, A., et al; "Scaffolds That Mimic Antigen-Presenting Cells Enable Ex Vivo Expansion of Primary T Cells"; Nature Biotechnology vol. 36, No. 2, Feb. 2018.

Choi, S., et al; "Alzheimer's Disease and Stem Cell Therapy"; Experimental Neurobiology 2014, vol. 23(1), pp. 45-52.

Dynabeads™ Human T-Activator CD3/CD28 for T Cell Expansion and Activation <<https://www.thermofisher.com/order/catalog/product/11161D>> accessed Aug. 30, 2018.

Elkasabi, Y., et al; "Towards Multipotent Coatings: Chemical Vapor Deposition and Biofunctionalization of Carbonyl-Substituted Copolymers"; Macromolecular Rapid Communications 2008, 29(11): pp. 855-870.

Fenge, C., et al; Sartorius Stedim Biotech; Large-Scale Perfusion and Concentrated Fed-Batch Operation of BIOSTAT® STR Single-Use Bioreactor.

Frith, J., et al; "Dynamic Three-Dimensional Culture Methods Enhance Mesenchymal Stem Cell Properties and Increase Therapeutic Potential"; Tissue Engineering Part C, Methods 2010, vol. 16(4): 735-749.

Gardel, L., et al; "A Novel Bidirectional Continuous Perfusion Bioreactor for the Culture of Large-sized Bone Tissue-engineered

(56) References Cited

OTHER PUBLICATIONS

Constructs"; Society for Biomaterials, Journal of Biomedical Materials Research B: Applied Biomaterials; Nov. 2013, vol. 10 1B, Issue 8, pp. 1377-1386.
General Electric Wave Bioreactor Systems, Cell Culture Procedures <<www.gelifesciences.com/wave>> accessed Apr. 18, 2017.
Glavaski-Joksimovic, A., et al; "Mesenchymal Stem Cells and Neuroregeneration in Parkinson's Disease", Experimental Neurology 2013, vol. 247, pp. 25-38.
Gordon, G., et al; "The Chemistry of Chlorine Dioxide"; Progress in Inorganic Chemistry 1972, vol. 15: pp. 201-286.
Han, Y, et al; "High-Performance Nano-Photoinitiators with Improved Safety for 3D Printing"; ACS Applied Materials and Interfaces 2017, 9(38): pp. 32418-32423.
Higuera, G., et al; "The Physics of Tissue Formation with Mesenchymal Stem Cells"; Trends in Biotechnology, Nov. 2012, vol. 30, No. 11; pp. 583-590.
Kaiser, A., et al; "Towards a Commercial Process for the Manufacture of Genetically Modified T Cells for Therapy"; https://www.nature.com/articles accessed Mar. 26, 2018.
Kim J. et al; "Bioreactor Strategy in Bone Tissue Engineering: Pre-Culture and Osteogenic Differentiation Under Two Flow Configurations"; Tissue Engineering: Part A 2012, vol. 18, Nos. 21-22: pp. 2354-2364.
Ko, H, et al; "One Step Immobilization of Peptides and Proteins by Using Modified Parylene with Formyl Groups"; Biosensors and Bioelectronics 2011, 30(1): pp. 56-60.
Kumar, A, et al; "Human Mesenchymal Stem Cells Expansion on Three-Dimensional (3D) Printed Poly-Styrene (PS) Scaffolds in a Perfusion Bioreactor"; Science Direct 2017, vol. 65, pp. 115-120.
Kumar, A., et al "Large Scale Industrialized Cell Expansion Producing the Critical Raw Material for Biofabrication Processes"; Biofabrication 7(4): 044103 (2015).
Kwon, T., et al; "Microfluidic Cell Retention Device for Perfusion of Mammalian Suspension Culture"; Scientific Reports 7:6703, 2017; <<https://www.nature.com/articles/s41598-017-06949-8>> accessed Mar. 26, 2018.
Lechanteur, C., et al "Large-Scale Clinical Expansion of Mesenchymal Stem Cells in the GMP-Compliant, Closed Automated Quantum® Cell Expansion System: Comparison with Expansion in Traditional T-Flasks"; Journal of Stem Cell Research & Therapy 2014, 04(08).
Ligon, S. et al; "Polymers for 3D Printing and Customized Additive Manufacturing", Chemical Reviews 2017, 117(15): pp. 10212-10290.
Mirro, R., "An Update on the Advantages of Fibra-Cel® Disks for Cell Culture"; eppendorf, Application Note No. 313, Jul. 2011.
Papadimitropoulos, A., et al; "Expansion of Human Mesenchymal Stromal Cells From Fresh Bone Marrow in a 3D Scaffold-Based System Under Direct Perfusion"; PLOS ONE, Jul. 2014, vol. 9, Issue 7.
Portner, R., et al; "Fixed Bed Reactors for the Cultivation of Mammalian Cells: Design, Performance and Scale-Up"; The Open Biotechnology Journal, 2007, 1, 41-46.
Provin, C., et al "A Method for the Design of 3D Scaffolds for High-Density Cell Attachment and Determination of Optimum Perfusion Culture Conditions"; Journal of Biomechanics 41 (2008) 1436-1449.
Sailon, A., et al "A Novel Flow-Perfusion Bioreactor Supports 3D Dynamic Cell Culture"; Journal of Biomedicine and Biotechnology, vol. 2009, Article ID 873816.
Schop, D., et al "Expansion of Mesenchymal Stem Cells Using a Microcarrier-based Cultivation System: Growth and Metabolism"; Journal of Tissue Engineering and Regeneration Medicine; 2008, 2L 126-135.
Sobral, JM et al "Three-Dimensional Plotted Scaffolds With Controlled Pore Size Gradients: Effect of Scaffold Geometry on Mechanical Performance and Cell Seeding Efficiency" Acta Biomaterialia, vol. 7, Issue 3, Mar. 2011, pp. 1009-1018 cited as Y PCT/US17/30833 in the ISR & WO, date of mailing Aug. 2, 2017 (10 pgs).

Specialty Coating Systems Parylene Properties <<https://scscoatings.com/docs/brochures/parylene_properties.pdf>> accessed Aug. 30, 2018.
Tan, C., et al; "Surface Engineering and Patterning Using Parylene for Biological Applications"; Materials 2010, 3(3): pp. 1803-1832.
Van Den Driesche, S., et al; "3D Printing Solutions for Microfluidic Chip-to-World Connections"; Micromachines 2018, 9: 71 (12 pgs).
Vitale, A., et al; "Frontal Conversion and Uniformity in 3D Printing by Photopolymerisation", . Materials 2016, 9(760), 13 pgs.
Weber, C. et al (2010) Production Process for Stem Cell Based Therapeutic Implants: Expanson of the Production Cell Line and Cultivation of Encapsulated Cells. Retrieved from http://krex.ksu.edu.
Wellinghoff, S., et al; Advanced Dental Restorative Composites Utilizing Low Polymerization Shrinkage Liquid Crystalline Monomers. In: Physical Chemistry 2006. Belgrade, Serbia; 2006, (8 pgs).
Wen, Z., et al "Repair Mechanisms of Bone Marrow Mesenchymal Stem Cells in Myocardial Infarction". Journal of Cellular and Molecular Medicine 2011, vol. 15, No. 5, pp. 1032-1043.
Whitford, W., et al "Single-Use, Continuous Processing of Primary Stem Cells"; BioProcess International, Cell Therapy Processing; Mar. 2014, 12(3):26-33.
Wu, H., et al; "Mesenchymal Stem Cell-based Therapy for Type 1 Diabetes"; Discovery Medicine 2014, vol. 17(93); pp. 139-143.
Yamada, S., et al; "Multi-Sized Sphere Packing"; <<http://www2.latech.edu/-jkanno/packing.pdf>>; dated Jul. 4, 2009; pp. 7-8 cl20; cited as Y in the ISR & WO, date of mailing Aug. 2, 2017; of related application No. PCT/US17/30833.
Yang, S., et al: "Mussel-Inspired Encapsulation and Functionalization of Individual Yeast Cells"; Journal of the American Chemical Society, 133, 2795-2797, 2011.
Yeatts, A., et al; "Bioreactors to Influence Stem Cell Fate: Augmentation of Mesenchymal Stem Cell Signaling Pathways Via Dynamic Culture Systems"; Biochimica et Biophysica Acta 2013, 1830 (2); pp. 2470-2480.
Yourek, G, et al; "Shear Stress Induces Osteogenic Differentiation of Human Mesenchymal Stem Cells"; Regenerative Medicine 2010, vol. 5, No. 5; pp. 713-724.
Zhang, J., et al; "Fabrication of Three Dimensional Polymeric Scaffolds With Spherical Pores"; J. Mater Sci 41 (2006) pp. 1725-1731 cited as A in PCT/US18/31027 ISR/WO mailed Jul. 23, 2018.
ISR & WO issued in PCT/US2017/30833, date of mailing Aug. 2, 2017 (14 pgs).
ISR & W/O mailed Jul. 23, 2018 (issued in related PCT/US18/31027 (9 pgs).
MAS.865 2018 "How to Make Something that Makes (almost) Anything"; <<http://fab.cba.mit.edu/classes/865.18/additive/multiphoton-polymerization/index.html>> (accessed Mar. 30, 2020; 10 pgs).
Geng, Qiang, et al; "Ultrafast Multi-focus 3-D Nano-fabrication Based on Two-photon Polymerization" <<https://www.nature.com/articles/s41467-019-10249-2>> (accessed Mar. 30, 2020; 7 pgs).
"Think Big. Print Nano. Your Partner for High-precision Additive Manufacturing"<<https://www.nanoscribe.com/en/>> (accessed Mar. 30, 2020; 7 pgs).
"Wide Range of Applications in Research, Prototyping and Production Processes Nanoscribe " <<https://www.nanoscribe.com/en/applications>> (accessed Mar. 30, 2020; 11 pgs).
Choi, et al "Three-Dimensional Scaffolds for Tissue Engineering: The Importance of Uniformity in Pore Size and Structure" American Chemical Society, Langmuir Article published on Web Nov. 23, 2010, 26(24), pp. 19001-19006 **cited as X & Y in EP Appln No. 1779329.8 EESR; also cited in SG Appln No. 11201809805W 1st W/O**.
Lee, et al: "Three-Dimensional Cell Culture Matrices: State of the Art"; Tissue Engineering: Part B, vol. 14, No. 1, 2008, pp. 61-86 **cited as A in EP Appln No. 1779329.8 EESR**.
Petrie Aronin, C., et al: "Comparative Effects of Scaffold Pore Size, Pore Volume, and Total Void Volume on Cranial Bone Healing Patterns Using Microsphere-based Scaffolds" Journal of Biomedical Materials Research Part A, Wiley InterScience Periodicals, Inc. published online Apr. 28, 2008 pp. 632-641 **cited as A in EP Appln No. 1779329.8 EESR**.

(56) References Cited

OTHER PUBLICATIONS

Zeltinger, Ph.D., J., et al: "Effect of Pore Size and Void Fraction on Cellular Adhesion, Proliferation, and Matrix Deposition"; Tissue Engineering, vol. 7, No. 5, 2001, Mary Ann Liebert, Inc.; downloaded by EPO from <<www.lieberpub.com>> on Nov. 22, 2019 (pp. 557-572) **cited as A in EP Appln No. 1779329.8 EESR******.
Extended European Search Report issued in corresponding European Patent Appln No. 1779329.8; dated Dec. 5, 2019 (16 pgs).
1st Written Opinion issued in corresponding Singapore Appln No. 11201809805W; dated Feb. 4, 2020 (6 pgs).
International Search Report; dated Jan. 23, 2020; issued in related PCT/US2019/52719 (11 pgs).
Preliminary Report on Patentability dated Nov. 15, 2018, issued in PCT Patent Application No. PCT/US2017/030833, 12 pages.
Office Action dated Aug. 7, 2020, issued in U.S. Appl. No. 15/945,000, 14 pages.
Looby et al., Fixed bed porous glass sphere (porosphere) bioreactors for animal cells, Cytotechnology 1, Aug. 8, 1988, 339-346.
Intent to Grant dated Oct. 13, 2020, issued in European Patent Application No. 17793,249.8, 7 pages.
Preliminary Report on Patentability dated Oct. 15, 2020, issued in PCT Patent Application No. PCT/US2018/031027, 7 pages.
Sung-Wook Choi; et al, Neovascularization in Biodegradable Inverse Opal Scaffolds with Uniform and Precisely controlled Pore Sizes, NIH Public Access—Adv Healthe Mater, Jan. 2013: 2(1), 18 pages.
Office Action dated Jan. 18, 2021, issued in Japanese Patent Application No. 2018-558237, 5 pages.

\* cited by examiner

THREE-DIMENSIONAL BIOREACTOR FOR CELL EXPANSION AND RELATED APPLICATIONS

CROSS-REFERENCE TO RELATED APPLICATIONS

The present application claimed the benefit of the filing date of U.S. Provisional Application No. 62/332,177, filed on May 5, 2016, the teachings of which are incorporated herein by reference.

FIELD OF THE INVENTION

The present disclosure relates to the design, fabrication, and applications of a three-dimensional (3D) bioreactor for cell expansion and cell derived substance production. The bioreactor is composed of non-random voids interconnected through non-random pores providing a continuous three-dimensional surface area for cell adherence and growth. Such 3D bioreactor is also scalable with a defined geometry, surface coating, and fluidic dynamics to maintain a monolayer cell culture and reduce or prevent cell aggregation, phenotype change, or extracellular production, and is particularly suitable for the expansion of stem cells, primary cells, and other adherent cells, or non-adherent cells under appropriate surface coating of the bioreactor.

BACKGROUND

With the recent development of stem cell technology and regenerative medicine, the number of stem cell-based therapies has increased significantly. Stem cells have the potential to cure many human diseases because they are not yet specialized, and can differentiate into many types of cells for tissue repair and regeneration. Well studied adult stem cells, such as mesenchymal stem cells (MSCs), can now be easily isolated from bone marrow, adipose tissue, placenta/umbilical cord, and peripheral blood. They have multipotency to differentiate into osteocytes, chondrocytes, and adipocytes for bone, cartilage, and skin regeneration.

MSCs are also found to secrete a broad spectrum of bioactive molecules including hormones, growth factors, cytokines, chemokines, and exosomes, which have potential therapeutic effects. Some known therapeutic effects of MSCs include immunomodulation, anti-apoptosis, angiogenesis, support of growth and differentiation of local stem progenitor cells, anti-scarring, and chemoattraction. These properties of stem cells are not only useful for them to be involved in cell-based therapies, but also for the manufacturing of biopharmaceuticals secreted by the cells.

In clinical applications, a typical therapeutic dose needs about $10^8$-$10^9$ stem cells (typically 2-20 million cells per kilogram of body weight). It is also known that one gram of tissue contains about $10^9$ cells. However, for the majority of clinical situations, cells collected from donors are not sufficient to meet the clinical need. Typically, a 30-50 mL bone marrow aspiration from the iliac crest of a donor contains about 600-1000×$10^6$ of bone marrow mononuclear cells (BMMCs), which include lymphocytes, monocytes, hematopoietic and endothelial progenitor cells, and MSCs. Among the BMMCs, only about 6-10×$10^4$ (or 0.01% or less) cells are surface adherent MSCs. A 10,000-fold cell expansion is needed from around $10^5$ MSCs collected from a donor to reach a clinical injection dose of $10^9$ cells.

Conventional MSC expansion has relied upon two-dimensional (2D) planar systems, identified as the tissue-culture flasks (T-flasks) or roller bottles which bathe the cells that are attached to the inner surface with a selected medium. Both systems are typically made of polystyrene with surface treatment (oxygen plasma) to improve cell attachment. A regular cell expansion process starts with a seeding density of 3×$10^3$ cells/cm$^2$ cells on the bottom of T-flask or on the wall of roller bottle. If a low seeding density is used, the cells will grow slowly, probably due to the lack of signals from neighborhood cells. After about 5-6 days of culture, cells form a monolayer on the culture surface and cover the entire culture area (called 100% confluence) and can reach cell densities around 0.50×$10^5$ cells/cm$^2$. When the cell reaches 100% confluence, they stop proliferation due to cell-cell contact inhibition and begin differentiation and develop an extracellular matrix. Cell differentiation can then alter the original cell phenotype. To reduce cell-cell contact (or aggregation), cell phenotype change, and formation of an extracellular matrix, the cells are usually harvested at 80% of confluence (or around cell density of 0.40×$10^5$ cells/cm$^2$). From the seeding density of 3×$10^3$ cells/cm$^2$ to the harvest density of 0.40×$10^5$ cells/cm$^2$ results a cell expansion of about 13 times.

The number of cells that can grow on T-flasks or roller bottles are proportional to the culture surface area. Therefore, T-flasks are named after their cell culture area as T-25, T-75, and T175, which indicate the cell culture area of 25, 75, and 175 cm$^2$, respectively. The 2D T-flask is difficult to scale-up to liter, tens of liter, or hundreds of liter levels with a reasonable footprint due to the low surface to volume ratio.

Furthermore, the culture process has to be step-by-step due to the seeding density requirements. That is, the $10^5$ cells from donor have to be expanded in a T-25 or T75 flasks at the first step. Then the expanded cells (~1.3×$10^6$) will be detached (dissociated from surface using enzyme) and then re-seeded to 5 to 6 of T-75 flasks for further expansion. From $10^5$ cells expanding to the clinical relevant $10^9$ cells, it needs over 120 T-75 flasks and three cell-detachment re-seeding processes. See FIG. 15. Each detachment of cells from one surface and re-seed (or sub-culture) onto a different surface is called a "passage". Handling a large number of T-flasks manually in cell expansion is not only expensive but also one that can easily introduce contamination.

Other three dimensional cell expansion strategies have been reported which include stacked plate, hollow fiber, microcarrier-based stirred reactors, wave bioreactors, rotating wall bioreactors, and fixed-bed bioreactors. Attention is directed to *Large-Scale Industrialized Cell Expansion: Producing The Critical Raw Material For Biofabrication Processes*, A. Kumar and B. Starly, Biofabrication 7 (4):044103 (2015). However, none of these existing 3D bioreactors can meet all the following preferred conditions for adherent cells, especially stem cell expansion: (1) relatively easy scale up and scale down; (2) able to scale up to hundreds or even thousands of liters for cell manufacturing; (3) mechanically stable, non-degradable structure to allow medium perfusion; (4) low shear stress to cells; (5) low gradient differential in nutrition and oxygen delivery; (6) prevention of cell-cell aggregation; (7) relatively smooth (and preferably pore-free) cell culture surfaces; (8) maintaining monolayer cell cultures; (9) easy cell dissociation from the culture surface to a single cell suspension; and (10) automatic and cost-effective cell manufacturing.

Accordingly, a need remains for methods and devices to improve cellular expansion, and in particular stem cell expansion, by offering improved bioreactor designs, cost-effective fabrication techniques, and improved bioreactor operating capability in order to achieve clinical application dose requirements.

SUMMARY

A 3D bioreactor for growth of cells, the bioreactor comprising a plurality of non-random interconnected voids, packed in 3D space in repeatable patterns, with a plurality of non-random pore openings between said voids. The bioreactor aims to achieve a maximum possible surface to volume ratio while the geometry is designed to maintain monolayer cell cultures, reduce or prevent high cell shear stress, cell aggregation, phenotype change, or extracellular production, and is particularly suitable for the expansion of stem cells.

In one embodiment, the present invention is directed at a 3D bioreactor for growth of cells comprising a plurality of voids having a surface area for cell expansion. The plurality of voids have a diameter D, a plurality of pore openings between the voids having a diameter d, such that D>d and wherein: (a) 90% or more of the voids have a selected void volume (V) that does not vary by more than +/−10.0%; and (b) 90% or more of the pore openings between the voids have a value of d that does not vary by more than +/−10.0%.

In another embodiment, the present invention is directed at a 3D bioreactor for growth of cells comprising a plurality of voids having a surface area for cell expansion. The plurality of voids have a diameter D of greater than 0.4 mm to 100.0 mm, a plurality of pore openings between the voids having a diameter d in the range of 0.2 mm to 10.0 mm, wherein D>d, further characterized in that: (a) 90% or more of said voids have a selected void volume (V) that does not vary by more than +/−10.0%; and (b) 90% or more of the pore openings between the voids have a value of d that does not vary by more than +/−10.0%, and the 3D bioreactor is formed from a material having a Tensile Modulus of at least 0.01 GPa.

In a still further embodiment, the present invention is directed at a 3D bioreactor for growth of cells comprising:
 a first and second plurality of voids having a surface area for cell expansion;
 said first plurality of voids having a diameter $D_1$, a plurality of pore openings between the first plurality of voids having a diameter $d_1$, wherein $D_1>d_1$, where 90% or more of the plurality of voids have a void volume ($V_1$) with a tolerance that does not vary by more than +/−10.0%;
 said second plurality of voids having a diameter $D_2$, a plurality of pore openings between the second plurality of voids having a diameter $d_2$ wherein $D_2>d_2$, wherein 90% of the second plurality of voids have a void volume ($V_2$) with a tolerance that does not vary by more than +/−10.0%; and
 the values of $V_1$ and $V_2$ are different and outside of said tolerance variations such that $$[V_1 +/-10.0\%] \neq [V_2 +/-10.0\%].$$

The present invention also relates to a fabrication or manufacturing method of forming a 3D bioreactor comprising a plurality of voids having a surface area for cell expansion. One may therefore initially design/identify for the plurality of voids a targeted internal void volume ($V_t$) and also identify for the 3D bioreactor a targeted surface area ($SA_t$). This may then be followed by forming the 3D bioreactor with: (1) an actual void volume ($V_a$) for the one or more voids wherein $V_a$ is within +/−10.0% of $V_t$; and/or (2) an actual surface area ($SA_a$) of the 3D bioreactor wherein $SA_a$ is within +/−10.0% of $SA_t$.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF PREFERRED EMBODIMENTS

Figure 1:
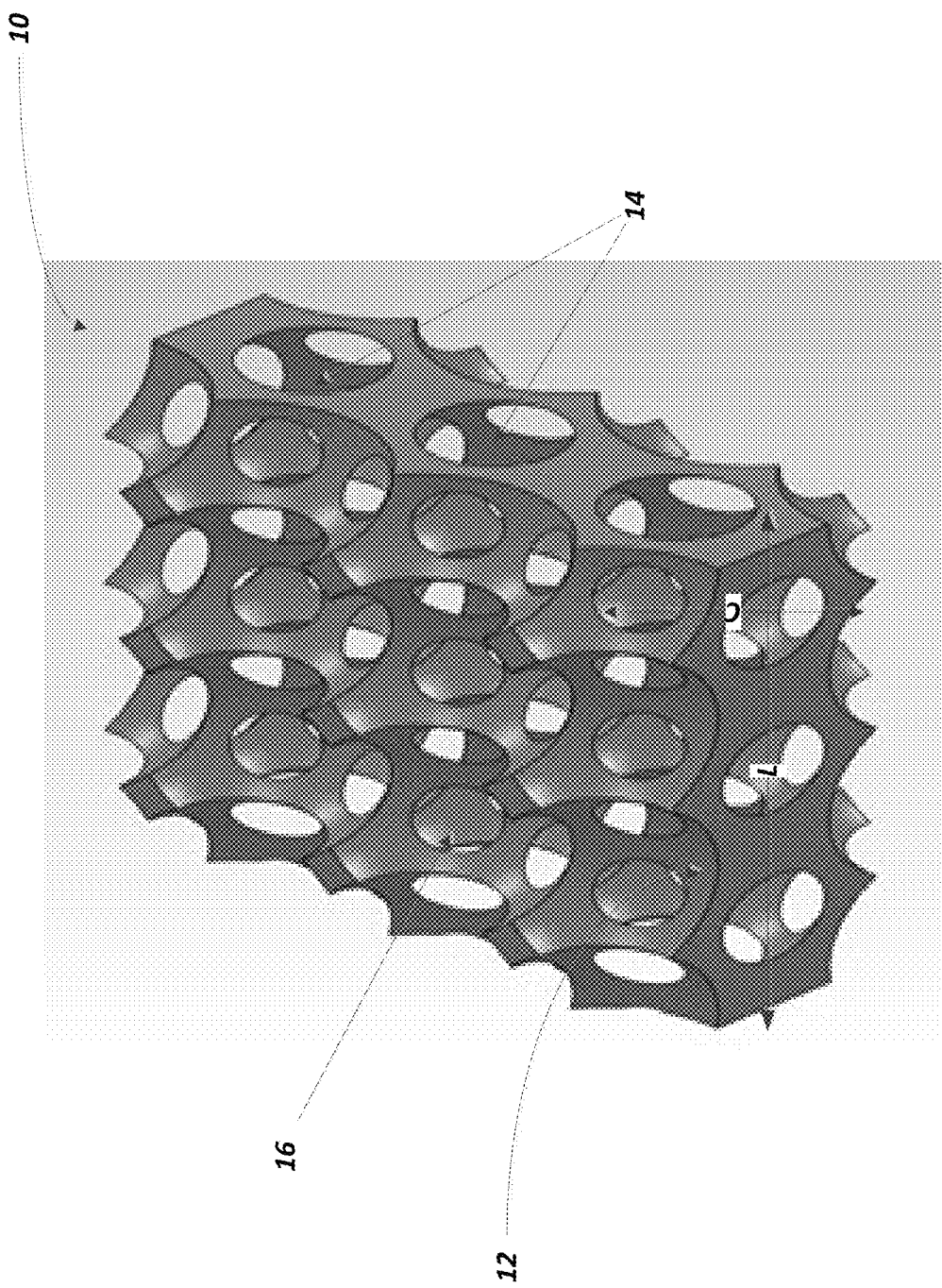
FIG. 1 illustrates a section view of the 3D bioreactor fixed-bed.

The present disclosure relates to a bioreactor design and with corresponding operating capability to achieve clinical cell expansion dosage requirements. Reference to a bioreactor herein refers to the disclosed 3D reactor in which biological and/or biochemical processes can be implemented under selected environmental and operating conditions. This includes control of one or more of the following: geometry/size of the voids, interconnected pore size between the voids and total number of voids included (determining the overall dimension of the bioreactor). In addition one may selective control surface coatings, flow characteristics through the voids within the bioreactor, pH, temperature, pressure, oxygen, nutrient supply, and/or waste removal. Clinical dosage requirements is reference to the ability to provide a dose of $10^9$ cells or greater.

The 3D bioreactor herein is one that preferably provides cellular expansion from a relatively low number of donor cells to the clinical dose requirements that also can reduce or eliminate culture passages and related MSC phenotype alterations. The 3D bioreactor's preferred fixed-bed 10 is generally illustrated in cut-away view in FIG. 1, which shows an example of a preferred packed and spherical void structure and their interconnected pores between the spherical voids.

More specifically, the bioreactor includes a continuous interconnected 3D surface area 12 that provides for the ability for the cells to adhere and grow as a monolayer and also defines within the bioreactor a plurality of interconnected non-random voids 14 which as illustrated are preferably of spherical shape with internal concave surfaces to maximize the surface to volume ratio. A void is understood as an open space of some defined volume. By reference to non-random it should be understood that one can now identify a targeted or selected number of voids in the 3D bioreactor that results in an actual repeating void size and/or geometry of a desired tolerance.

By reference to a continuous surface, it is understood that the expanding cells can readily migrate from one surface area location into another within the 3D bioreactor, and the surface does not include any random interruptions, such as random breaks in the surface or random gaps of 0.1 mm or more. Preferably, 50% or more of the surface area within the 3D bioreactor for cell expansion is a continuous surface, more preferably, 60% or more, 70% or more, 80% or more, 90% or more, 95% or more or 99% or more of the surface area within the 3D bioreactor is continuous.

In addition, the bioreactor fixed-bed 10 includes non-random interconnecting pore openings 16 as between the voids. Again, reference to non-random should be understood that one can now identify a targeted or selected number of pores for the voids, of a selected pore diameter, that results in an actual number of pores having pore diameters of a desired tolerance. The bioreactor as illustrated in cut-away view also ultimately defines a layer of non-random voids (see arrow "L") and it may be appreciated that the multiple layers of the bioreactor may then allow for identification of a plurality of such non-random voids within a column (see arrow "C").

The bioreactor may be made of biocompatible or bio-inert polymeric materials such as polystyrene, polycarbonate, acrylonitrile-butadiene-styrene (ABS), polylactic acid (PLA), polycaprolactone (PCL) used in FDM (fused deposition modeling) 3D printing technology. Reference to biocompatible or bio-inert should be understood as a material that is non-toxic to the culturing cells. In addition, the polymeric materials for the 3D bioreactor are preferably selected from those polymers that at not susceptible to hydrolysis during cell cultivation, such that the amount of hydrolysis does not exceed 5.0% by weight of the polymeric material present, more preferably it does not exceed 2.5% by weight, and most preferably does not exceed 1.0% by weight. The bioreactor may also be made of biocompatible photosensitive materials (e.g., Pro3Dure, Somos WaterShed XC 11122, etc.) used in SLA (stereolithography) and DLP (digital light processing) 3D printing technologies.

It is preferable that the material used to fabricate the bioreactor is not degradable in aqueous medium and can provide a mechanical stable structure to tolerate aqueous medium flow during cell expansion. It is preferable that the material and manufacturing process can result a solid and smooth interconnected surface area for monolayer cell expansion. By reference to a solid surface, it should be understood that the surface is such that it will reduce or prevent penetration or embedding by the culturing cells, which typically have a diameter of about 20 microns to 100 microns. Preferably, the 3D bioreactor herein is one that has a surface that has a surface roughness value (Ra), which is reference to the arithmetic average of the absolute values of the profile height deviations from the mean line, recorded within an evaluation length. Accordingly, it is contemplated herein that Ra of the 3D bioreactor surface will have a value of less than or equal to 20 μm, more preferably, less than or equal to 5 μm.

The 3D bioreactor herein is also preferably one that is formed from material that indicates a Shore D Hardness of at least 10, or in the range of 10-95, and more preferably in the range of 45-95. In such regard, it is also worth noting that the 3D bioreactor herein is one that does not make use of a hydrogel type structure, which may be understood as a hydrophilic type polymeric structure, that includes some amount of crosslinking, and which absorbs significant amounts of water (e.g., 10-40% by weight). It is also worth noting that the 3D bioreactor herein is one that preferably does not make use of collagen, alginate, fibrin and other polymers that cells can easily digest and undergo remodeling.

Furthermore, the 3D bioreactor herein is preferably one that is made from materials that have a Tensile Modulus of at least 0.01 GPa. More preferably, the Tensile Modulus has a value that is in the range of 0.01 GPa to 20.0 GPa, at 0.01 GPa increments. Even more preferably, the Tensile Modulus for the material for the 3D bioreactor is in the range of 0.01 GPa to 10.0 GPa or 1.0 GPa to 10 GPa. For example, with respect to the earlier referenced polymeric materials suitable for manufacture of the 3D bioreactor herein, polystyrene indicates a Tensile Modulus of about 3.0 GPa, polycarbonate at about 2.6 GPa, ABS at about 2.3 GPa, PLA at about 3.5 GPa and PCL at about 1.2 GPa.

The 3D bioreactor design herein with such preferred regular geometric characteristics and continuous surface area is preferably fabricated by additive manufacturing technologies, such as FDM, selective laser sintering (SLS), stereolithography (SLA), digital light processing (DLP) 3D printing technologies, etc., according to computer generated designs made available by, e.g., a SolidWorks™ computer-aided design (CAD) program.

By way of preferred example, the process utilizing Solid-Works™ to create the 3D bioreactor design is described below. A computer model for the bioreactor negative is initially created. More specifically, what may therefore be described as a 3D bioreactor negative was created, e.g., using packed 6.0 mm diameter spheres that overlap to create 1.0 mm diameter connecting pores between spheres. Of course, other possible dimensions are contemplated within the broad context of this disclosure.

The spheres are preferably organized in a hexagonal close packed (HCP) lattice to create an efficiently (or tightly) packed geometry that results in each sphere surrounded by 12 neighborhood spheres. A unit cell of this exemplary geometry is shown in FIG. 1a. More specifically, in FIG. 1a there is a unit cell of the HCP lattice where the top three spheres are displayed as translucent to show the 6 radial overlapping areas between the neighborhood spheres. The pores are formed at these overlapping areas. Preferably, the maximum number of pores is 12 to optimize packing. The minimum pore number is 2 in order to allow medium perfusion through the voids of the 3D bioreactor. Accordingly, at least 90.0% to 100% of the voids present in the 3D bioreactor have at least 2 pore openings per void. More preferably, at least 90.0% to 100% of the voids in the 3D bioreactor have 8-12 pore openings per void. In one particularly preferred embodiment, at least 90.0% to 100% of the voids in the 3D bioreactor have 12 pore openings per void.
between adjacent voids within the plurality of voids present, and more preferably, there are 8-12 interconnected pore openings between the adjacent voids, and in one particularly preferred embodiment, there are 12 pore openings between the adjacent voids.

Figure 1B:
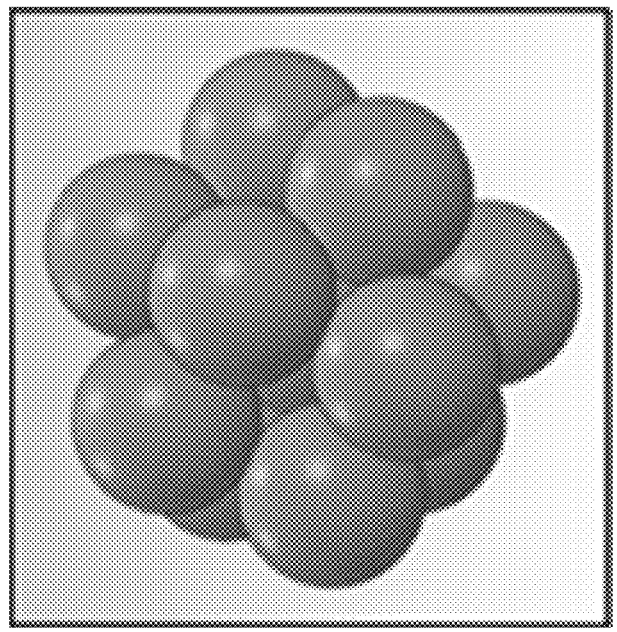
FIG. 1b illustrates a unit negative model with each sphere surrounded by 12 identical neighborhood spheres.
Figure 1A:
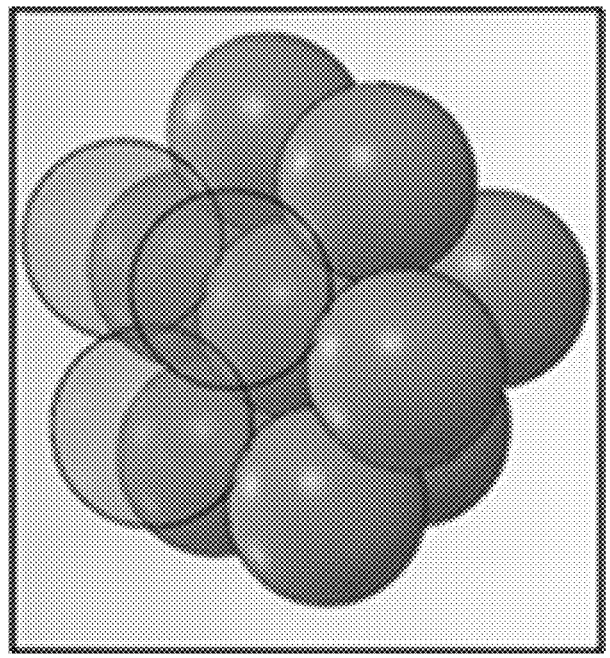
FIG. 1a illustrates a unit negative model of the bioreactor that shows the overlapping of the neighborhood spheres.
Figure 1D:
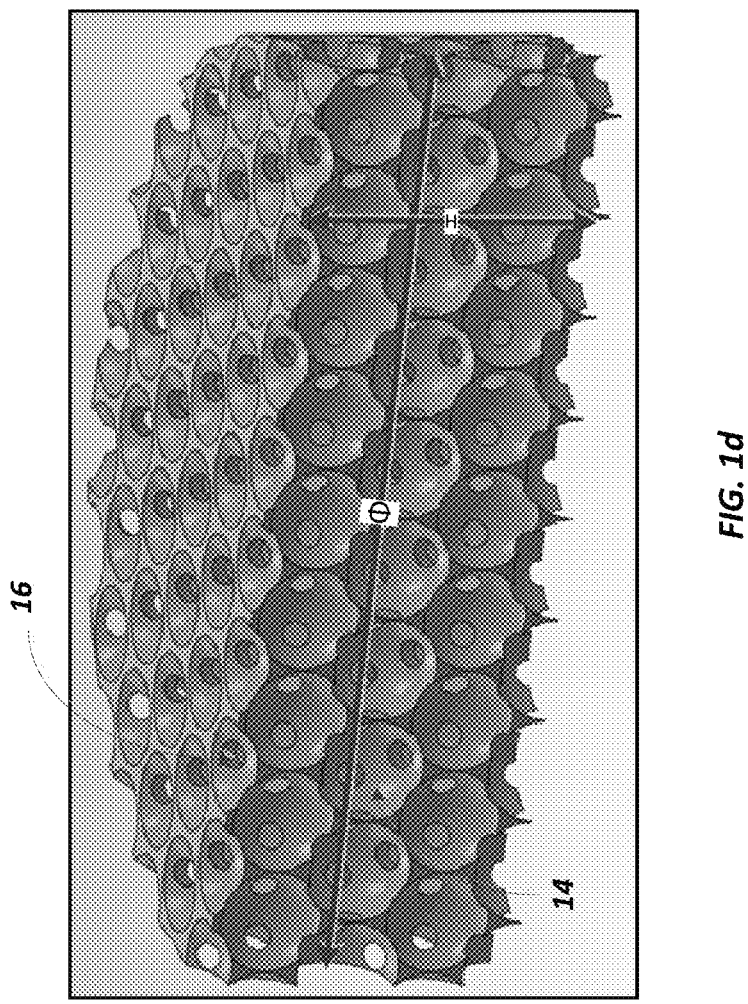
FIG. 1d illustrates a 3D bioreactor fixed-bed geometry in cross-sectional view.
Figure 1C:
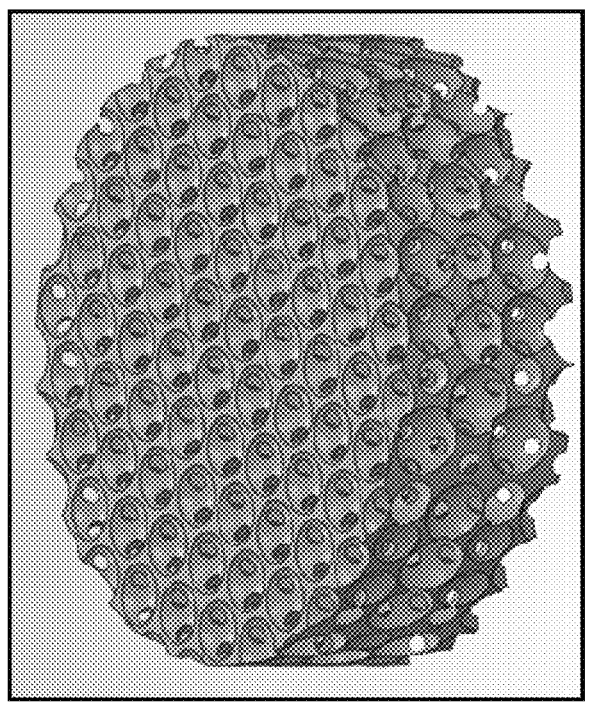
FIG. 1c illustrates a 3D bioreactor fixed-bed geometry showing an interconnected void system.

In FIG. 1b, all spheres of the unit are illustrated. The bioreactor geometry is then preferably created by reversing the negative model to create the positive model comprising an interconnected spherical void system shown in FIG. 1c. Moreover, in FIG. 1d one can see the 3D bioreactor again in cross-sectional view providing another illustration of the interconnected voids shown in cut-away view at 14 with regular geometric characteristics (substantially the same control of void volume as described above) and the corresponding interconnected pore openings 16.

Figure 1E:
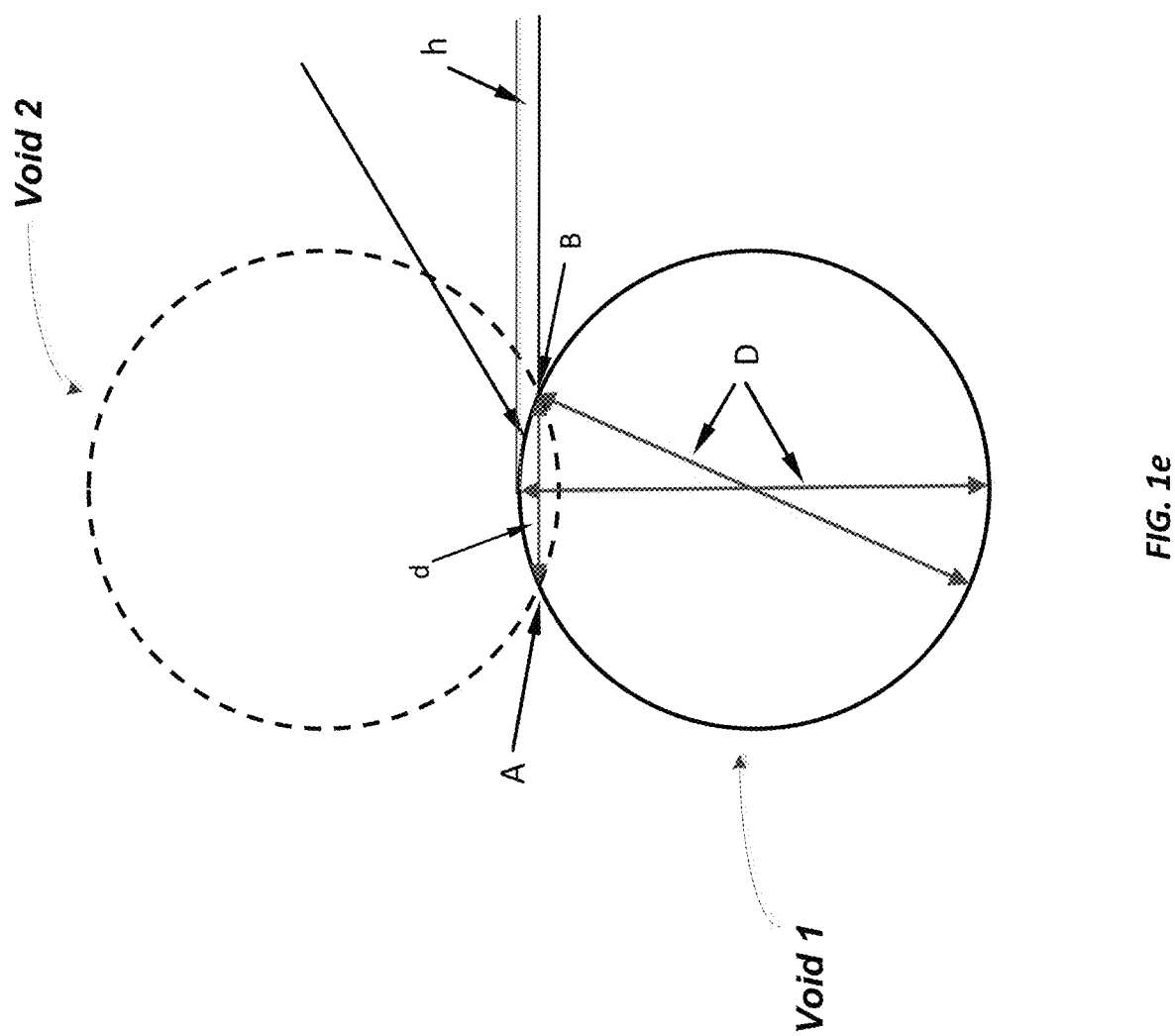
FIG. 1e illustrates in 2D view the identified spherical voids of a 3D bioreactor, and their overlapping areas to form interconnected pores between the spherical voids.

In the preferred regular geometric 3D bioreactor described above, one can identify a relationship as between the void diameter and interconnected pore diameter. Attention is directed to FIG. 1e. For this preferred geometry, Spherical Void 1 is represented by a solid circle, diameter is D (indicated by the arrows). Diameter "D" may therefore be understood as the longest distance between any two points on the internal void surface. Spherical Void 2 is represented by a dash circle and would also have diameter D (not shown). Spherical Void 2 is one of the 12 of neighborhood voids of Spherical Void 1. Due to the overlap between the neighborhood voids, it forms interconnected pores between the spherical voids, with the diameter of "d" as also indicated by the generally horizontal arrow. Diameter "d" may therefore be understood as the longest distance between any two points at the pore opening. The total 3D spherical surface area of the void is $SA_{void}=4\times\pi\times(D/2)^2$. The surface area between A and B, called $S_{cap}=\pi\times D\times h$, where $$h = \frac{D - \sqrt{D^2 - d^2}}{2}.$$

The useful void surface for a given void in the 3D bioreactor would be $SA_u = SA_{void} - [12\times S_{cap}]$.

The smaller the void diameter D, the larger the number of voids can be packed into a set 3D space (volume), and therefore results larger overall cell culture surface. However, to minimize or prevent cell aggregation (which as discussed herein can inhibit cell growth and induce cell phenotype change), the minimal diameter of the pores d=0.2 mm for this geometry. The diameter of the pores d may fall in the range of 0.2 mm to 10 mm and more preferably 0.2 mm to 2.0 mm. Most preferably, d≥0.5 mm and falls in the range of 0.5 mm to 2.0 mm.

If D=0.40 mm or less, the computed $SA_u$ is less than 0 when d=0.2 mm, which leads to an impossible structure therefore, D has to be >0.4 mm for this 3D bioreactor geometry. However, D can have a value between 0.4 mm to 100.0 mm, more preferably, 0.4 mm to 50.0 mm, and also in the range of 0.4 mm to 25.0 mm. One particularly preferred value of D falls in the range of 2.0 mm to 10.0 mm. Spherical voids with a relatively large value of D may reduce the objective of increasing cell culture surface area as much as possible within a same bioreactor volume. Accordingly, for the preferred geometry illustrated in FIG. 1E, D>0.4 mm (the diameter of the void) and d>0.20 mm (the diameter of the pores). It is also worth noting that with respect to any selected value of diameter D for the voids in the range of 0.4 mm to 100.0, and any selected value of diameter d for the pores in the range of 0.2 mm to 10.0 mm, the value of D is such that it is greater than the value of d (D>d).

It can now be appreciated that the 3D bioreactor herein can be characterized with respect to its non-random characteristics. Preferably, all of the voids within the 3D bioreactor are such that they have substantially the same volume to achieve the most efficient 3D space packing and offer the largest corresponding continuous surface area. With respect to the total number of interconnected voids present in any given 3D bioreactor, preferably, 90.0% or more of such voids, or even 95.0% or more of such voids, or even 99.0% to 100% of such voids have a void volume (V) whose tolerance is such that it does not vary by more than +/−10.0%, or +/−5.0%, or +/−2.5% or +/−1.0%, or +/−0.5% or +/−0.1%. It should be noted that while the voids in FIG. 1 are shown as generally spherical, other voids geometries are contemplated. The diameter of voids are chosen to minimize or avoid cell aggregation and to provide maximum useful surface area for cell culturing.

Another non-random characteristic of the 3D bioreactor herein are the pore openings between the voids, having a diameter d (see again FIG. 1e). Similar to the above, 90.0% or more of the pore openings, or even 95.0% or more of the pore openings, or even 99.0% to 100% of the pore openings between the voids, indicate a value of d whose tolerance does not vary more than +/−10.%, or +/−5.0%, or +/−2.5% or +/−1.0%, or +/−0.5% or +/−0.1%.

It can therefore now by appreciated that the 3D bioreactor herein for growth of cells comprises a surface area for cell expansion, a plurality of voids having a diameter D (the longest distance between any two points on the internal void surface), a plurality of pore openings between said voids having a diameter d (the longest distance between any two points at the pore opening), where D>d. In addition, 90% or more of the voids have a void volume (V) that does not vary by more than +/−10.0%, and 90% or more of the pore openings have a value of d that does not vary by more than +/−10.0%.

In addition, the 3D bioreactor herein for growth of cells can include a first plurality of voids having a diameter $D_1$, a plurality of pore openings between said first plurality of voids having a diameter $d_1$, wherein $D_1 > d_1$, where 90% or more of the first plurality of voids have a void volume ($V_1$) with a tolerance that does not vary by more than +/−10.0%. Such 3D bioreactor may also have a second plurality of voids having a diameter $D_2$, a plurality of pore openings between said second plurality of voids having a diameter $d_2$ wherein $D_2 > d_2$, wherein 90% of the second plurality of voids have a void volume ($V_2$) with a tolerance that does not vary by more than +/−10.0%. The values of $V_1$ and $V_2$ are different and outside of their tolerance variations. Stated another way, the value of $V_1$, including its tolerance of +/−10.0% and the value of $V_2$, including its tolerance of +/−10.0%, are different, or $[V_1 +/- 10.0\%] \neq [V_2 +/- 10.0\%]$.

The radius of curvature (Rc) of the surface within the voids is therefore preferably 1/0.5(D), or 1/0.2 mm=5 mm$^{-1}$ or lower. Preferably, Rc may have a value of 0.2 mm$^{-1}$ to 1.0 mm$^{-1}$, which corresponds to a value of D of 10.0 mm to 2.0 mm. A high curvature (large Rc) surface provides a significantly different environment than the typical monolayer 2D culture, which may also induce cell phenotype changes.

Cells are preferably seeded on the interconnected spherical void surfaces of the 3D bioreactor. Such 3D structure is preferably scalable and is able to provide a relatively high surface to volume ratio for relatively large cell expansion with a relatively small footprint cell expansion bioreactor. The surface area-to-volume ratio is also preferably determined by the diameter of the spherical voids. The smaller is the diameter, the higher is the surface area-to-volume ratio. Preferably, the voids provide a relatively "flat" surface (i.e., low radius of curvature≤1.0 mm$^{-1}$) for growth of cells having a size of 20 μm to 100 μm and also to reduce or avoid cell aggregation. In addition, as alluded to above, cell aggregation is also reduced or avoided by controlling the diameter d of the interconnected pores, which diameter is preferably at least 500 μm, but as noted, any size greater than 200 μm.

Figure 2:
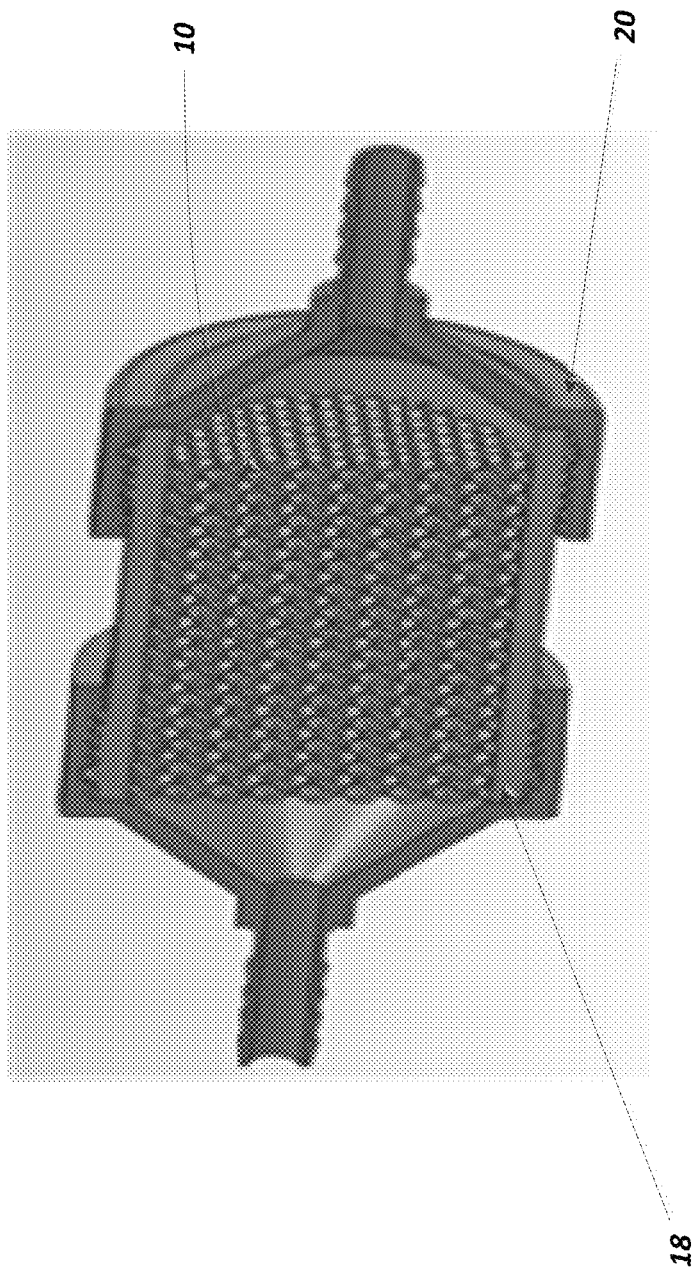
FIG. 2 illustrates a 3D bioreactor fixed-bed positioned in a housing with inlet and outlet for fluid perfusion.
Figure 3:
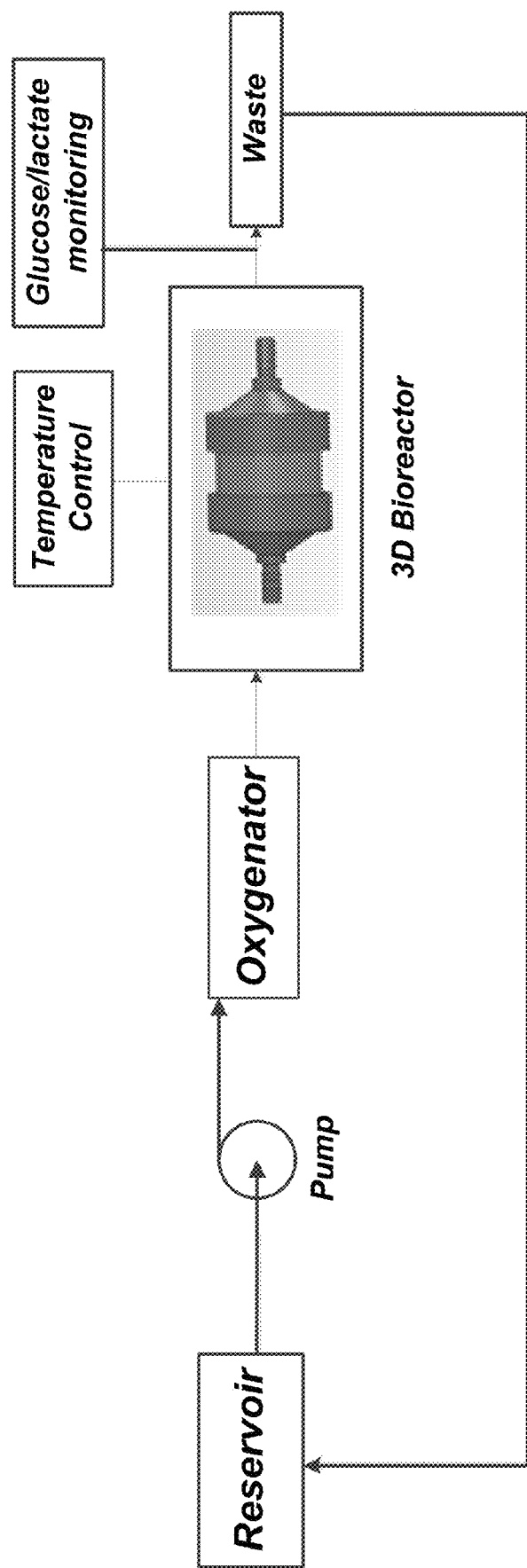
FIG. 3 illustrates a typical 3D bioreactor perfusion system.

The bioreactor fixed-bed 10 may therefore preferably serve as a single-use 3D bioreactor as further illustrated in FIG. 2. More specifically, the bioreactor 10 may be positioned in a housing 18 and then placed in the inlet and outlet compartment 20 for which inflow and outflow of fluid may be provided. Preferably, the bioreactor 10, housing 18, and the inlet and outlet compartment 20 can be fabricated as a single component using Additive Manufacturing technology. As shown in FIG. 3, the bioreactor 10 in housing 18 and inlet and outlet compartment 20 may become part of an overall 3D bioreactor system for MSCs expansion. More specifically, the 3D bioreactor is preferably positioned within a perfusion system which delivers a cell culture medium and oxygen through the 3D bioreactor for promoting cell growth. Multiple passage cell expansion methods used in 2D T-flask can also be directly applied to the 3D bioreactor except a 3D bioreactor has the cell culture area equivalent to 10s, 100s, or 1000s of T-flasks. Besides multiple passage cell expansion, a one-step expansion from a low number of donor cells to a clinically relevant number of cells is contemplated thus eliminating the multiple-passaging problem that induces MSC phenotype changes during expansion.

As may now be appreciated, the 3D bioreactor herein offers a relatively large surface-to-volume ratio depending upon the diameter of the interconnected voids. By way of example, a conventional roller bottle defining a cylinder of 5 cm diameter and 15 cm height, provides a cell growth surface area of 236 cm$^2$. If the same volume is used to enclose the 3D bioreactor herein with 2.0 mm diameter interconnected voids, a total of 44,968 spherical voids can be packed into the space, which can provide a matrix with about 5,648 cm$^2$ surface area, an almost 24-fold larger than the roller bottle surface area. In addition, while the roller bottle can only harvest around 9.4×10$^6$ cells, the equivalent volume 3D bioreactor herein is contemplated to harvest 2.2×10$^8$ cells.

At least one unique feature of the 3D bioreactor herein in comparison with hollow-fiber or microcarrier-based bioreactors is the ability to provide a large interconnected continuous surface instead of fragmented surfaces. Continuous surfaces within the 3D bioreactor herein are therefore contemplated to enable cells to more freely migrate from one area to another. The cells can then proliferate locally and at the same time gradually migrate out of the region to avoid cell-cell contact inhibition and differentiation. Using the perfusion system shown in FIG. 3, it is contemplated that one can readily create a gradient of nutrition or cell signals inside the bioreactor to induce cell migration into an open space while proliferating (as in a wound healing process).

The 3D bioreactor herein is also contemplated to allow one to seed a relatively low number of cells relatively evenly across the matrix surface. It is contemplated that the number of seeding cells can fall in the range of 30 to 3000 cells per square centimeter of useful void surface area, depending upon the size of the 3D bioreactor. Cells distributed in a 3D space within the 3D bioreactor herein can have a relatively large intracellular 2D separation to avoid direct cell-cell contact. At the same time it is possible to have a relatively short 3D separation distance (e.g., when cells reside on a spherical surface of opposite direction) enabling signals from nearby cells to be received.

In conjunction with the preferred 3D printing technology noted herein for preparation of the 3D bioreactor, computational fluid dynamics (CFD) can now be used to simulate the medium flow inside the bioreactor and estimate the flow rate and shear stress at any location inside the 3D interconnected surface, and allow for optimization to improve the cell culture environment. More specifically, CFD was employed to simulate the flow characteristics through the 3D interconnected voids of the bioreactor herein and to estimate the distribution of: (1) flow velocity; (2) pressure drop; and (3) wall shear stress. It may be appreciated that the latter parameter, shear stress, is important for cell expansion. A reduction in shear stress can reduce or prevent shear induced cell differentiation.

A small-scale (to increase computer simulation speed) cylindrical 3D bioreactor with a diameter of 17.5 mm, height of 5.83 mm, void diameter of 2 mm, and pore diameter of 0.5 mm was used in the simulations reported below. In this case, the diameter (101=17.5 mm) to height (H=5.83 mm) ratio of the bioreactor is 3:1 (FIG. 1*d*), which is a preferable ratio to reduce the gradient of nutrition and oxygen between the inlet and outlet of the bioreactor. Based on the cell density available on the fixed-bed spherical surface the oxygen and nutrition consumption rates were estimated, and how often the cell culture media needed to be replaced (i.e., the volume flow rate) was determined. An overall linear flow rate of 38.5 μm/sec was assumed in this simulation. Using 38.5 μm/sec rate laminar flow as the input to the 3D bioreactor, the CFD results are shown in FIGS. 4-6.

Figure 4E:
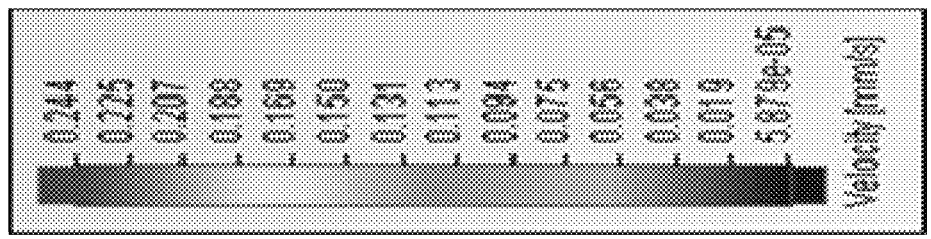
FIG. 4e indicates the scale of flow rate through a 3D bioreactor.

FIGS. 4*a*, 4*b*, 4*c* and 4*d* show the flow velocity profile throughout the small-scale cylindrical 3D bioreactor. FIG. 4*e* indicates the scale of flow rate. More specifically, FIG. 4*a* indicates the flow rate distribution viewed from the side of the bioreactor. The flow passes each spherical void through the pores along the flow direction. The white/gray areas in the figures are the solid regions between the spherical voids with no fluid flow. By comparing with the colored velocity scale bar in FIG. 4e, FIG. 4a indicates that the flow rate at the pores along the flow direction achieve the maximum flow rate of 200 μm/s to 240 μm/s. In contrast, the flow rates near the spherical surface reduce to a minimum of 0.06 μm/s to 19.0 μm/s, which will significantly reduce the flow caused shear stress to cells reside on the spherical surface.

Figure 4B:
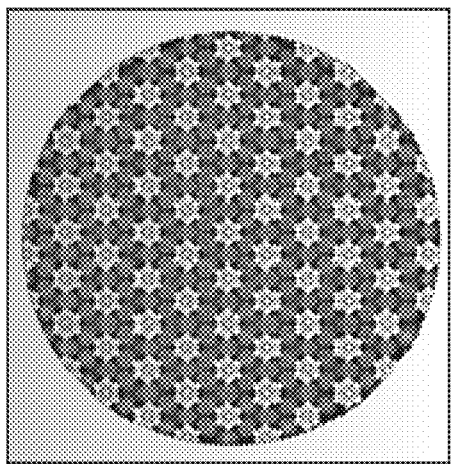
FIGS. 4a, 4b, 4c and 4d show flow rate profiles through a 3D bioreactor.

FIG. 4b indicates the velocity profile viewed from the top of the bioreactor through a center cross-section of the 3D structure. Again the image shows that the maximum rates are at each center of the pores of the spherical voids along the flow direction. This maximum rate is again in the range of 200 μm/s to 240 μm/s. The flow rate near spherical surface is again low and has a value of 0.06 μm/s to 19.0 μm/s.

Figure 4D:
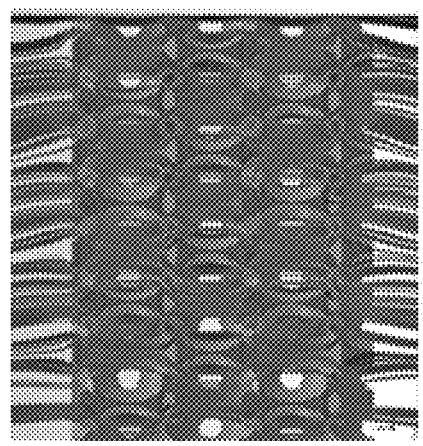
Figure 4A:
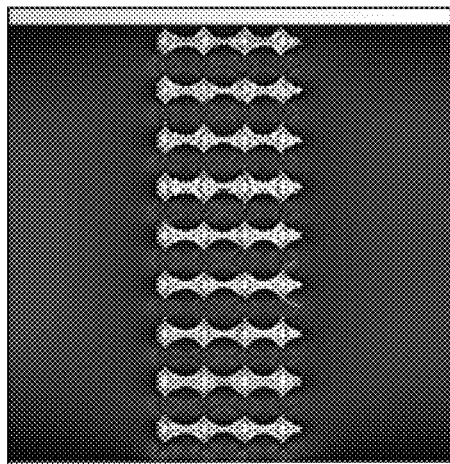
Figure 4C:
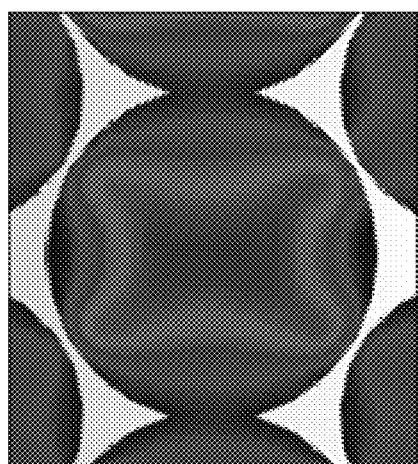

FIG. 4c indicates the velocity profile of an individual sphere void showing flow passing through the radial interconnected pores. FIG. 4c therefore provides a useful illustration of the flow distribution inside a spherical void. The high flow rate is at the central empty space of a void where there are no cells and is at a level of 200 μm/s to 240 μm/s. The cells reside on the concaved void surface where the flow rate is reduced and where the flow rate is again at a level of 0.06 μm/s to 19.0 μm/s. This unique structure can therefore shield cells from exposure to relatively high flow stress. This is another distinct advantage of the 3D bioreactor described herein over, e.g., micro-carrier based reactors, where cells are grown on the outside surface surfaces of 300 μm to 400 μm diameter microbeads with convex spherical surfaces that are suspended in a cell culture medium and stirred in a bioreactor to deliver nutrition and oxygen to the cells. Cells residing on such convex spherical surfaces can be exposed to relatively large shear stress to 0.1 Pa, which is known to affect cellular morphology, permeability, and gene expression. FIG. 4d indicates the flow trajectory through the side pores along the flow direction, indicating that the 3D bioreactor herein provides a relatively uniform flow pattern to provide nutrients and oxygen throughout.

Accordingly, the maximum linear flow rate computed inside the preferred 3D bioreactor is 200 μm/s to 240 μm/s which occurs at the 0.5 mm diameter interconnected pores between 2.0 mm diameter voids along the flow direction. As shown in FIGS. 4a-4e while the flow is preferentially in the central direction along the flow, there is still flow (~19.0 μm/sec) near the spherical surface to allow nutritional supply to the cells residing on the spherical surface. Therefore, it is contemplated that the cells are able to reside anywhere throughout the structure and thrive in any location because nutrients can be supplied both through flow convection and diffusion throughout the 3D bioreactor structure.

Figure 5C:
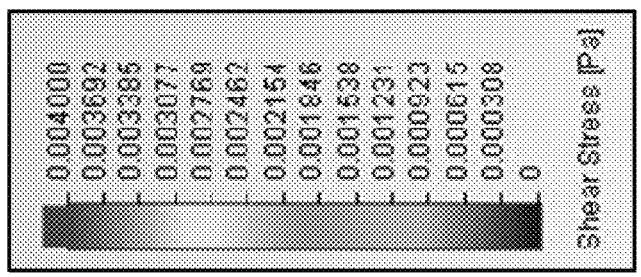
FIG. 5c indicates a scale of shear stress in unit Pa.
Figure 5B:
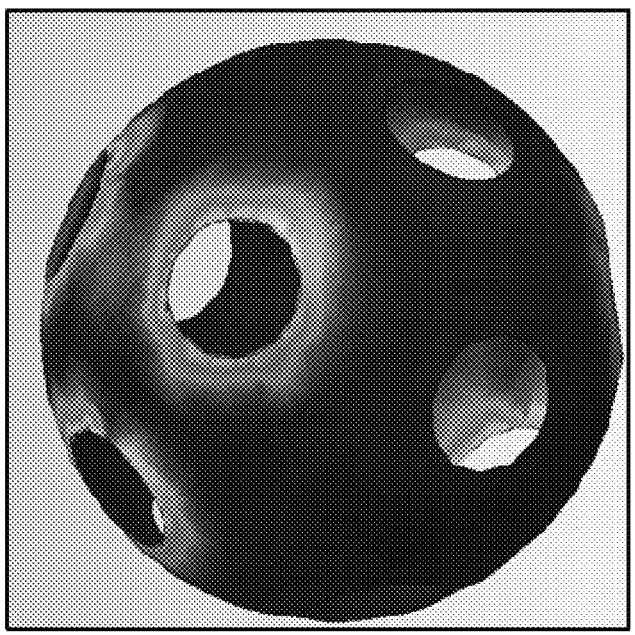
FIGS. 5a and 5b illustrate the distribution of surface shear stress in a 3D bioreactor.
Figure 5A:
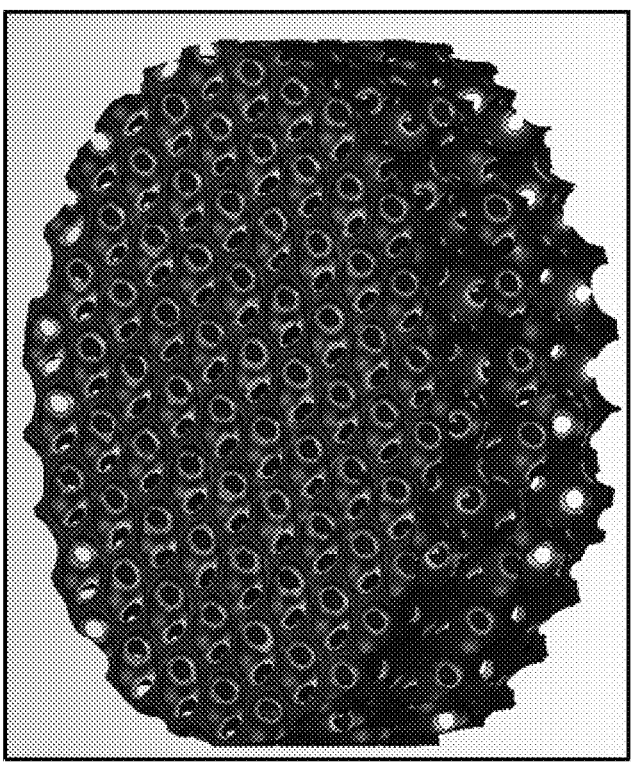

FIGS. 5a and 5b show the distribution of surface shear stress throughout the cylindrical 3D bioreactor described above as well as on a single spherical void surface. FIG. 5c indicates the scale of shear stress in units of Pa. The highest shear stress was observed on the edges of the interconnected pores. This is due to the higher flow rates at these locations. However, the majority of the useful spherical surface area within the bioreactor indicates a shear stress of less than $3 \times 10^{-4}$ Pa, which may be understood as 90% or more of the surface area of the bioreactor. This provides for cell proliferation, without shear induced differentiation. In addition, even the maximum shear stress of $4.0 \times 10^{-3}$ Pa, is believed to be lower than the average shear stress that cells experience when cultured in hollow fiber based bioreactors, wave bioreactors, and micro-carrier based bioreactors. Therefore, the 3D bioreactor herein is contemplated to provide a relatively lower shear stress environment for cell growth in comparison to existing cell expansion bioreactors. See, e.g., *Large-Scale Industrialized Cell Expansion: Producing The Critical Raw Material For Biofabrication Processes*, A. Kumar and B. Starly, Biofabrication 7(4):044103 (2015).

Figure 6B:
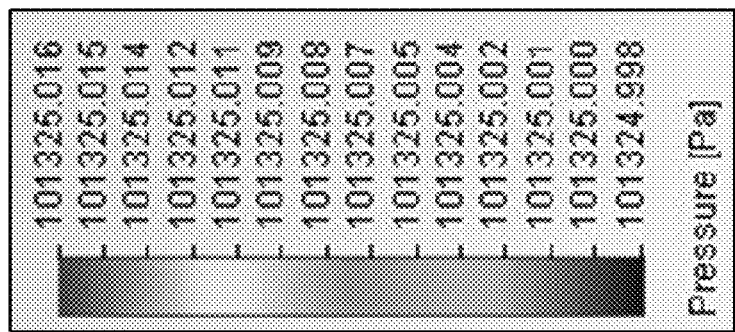
FIG. 6b indicates a scale of pressure.
Figure 6A:
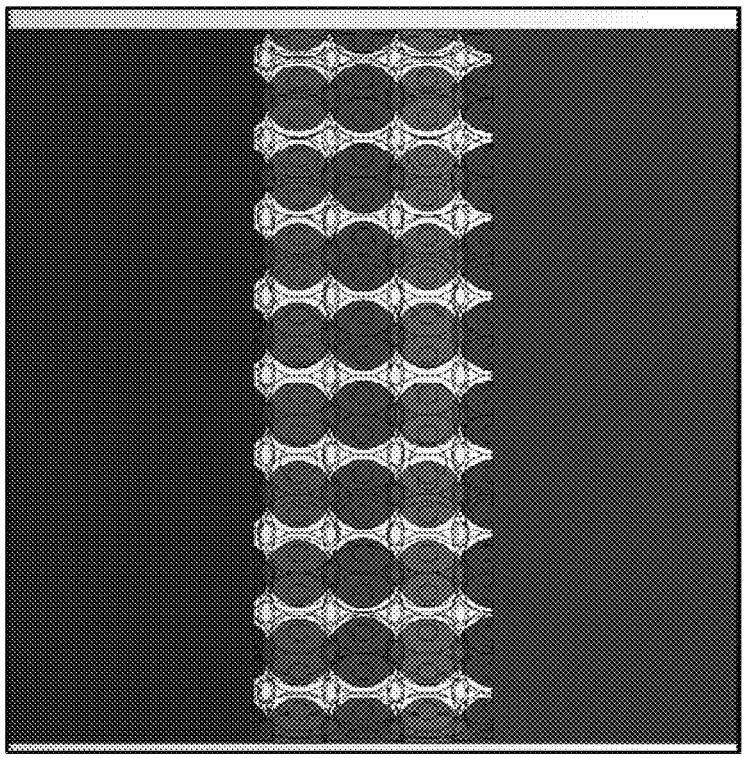
FIG. 6a illustrates the pressure drop (gradient) along the flow direction in a cylindrical 3D bioreactor.

FIG. 6a illustrates the pressure drop along the flow direction from bottom to the top of the cylindrical 3D bioreactor described above. FIG. 6b provides the applicable scale of pressure. The figure indicates that the overall pressure drop between the inlet and outlet of the bioreactor is less than or equal to 1.0 Pa. The pressure drop may therefore fall in the range of 0.1 Pa up to 1.0 Pa. In other words, cells near the inlet and outlet of the bioreactor will not experience significant differences in pressure. The low gradient of pressure suggests that such design will also produce a small gradient (or difference) in nutrition/metabolites concentrations between the inlet and outlet of the bioreactor. The low gradient is due to the design of the bioreactor such that the diameter Φ is larger than the height H while the total bioreactor volume remains the same. This is superior to the hollow fiber bioreactor. It is difficult to fabricate a hollow fiber bioreactor with Φ>H ratio to reduce the gradient of nutrition/metabolites between the inlet and outlet of the bioreactor.

A comparison was also made for the same total volume cylindrical 3D bioreactor with different aspect ratios (i.e. Φ:H ratio, Φ: overall diameter of the bioreactor fixed-bed, H: overall height of the bioreactor fixed-bed). See FIG. 1d. As shown in Table 1, for the same volume flow rate (volume flow rate=cross area of flow×linear velocity), the linear velocity increases significantly for a bioreactor with a low Φ:H ratio. The increase of linear velocity also increases the surface shear stress, pressure drop, as well as the gradient of nutrition/metabolites concentrations between the inlet and outlet, which would have an unfavorable effect for cell expansion. The disclosed fixed-bed 3D bioreactor is therefore preferably designed into a Φ:H ratio structure, e.g., a Φ:H ratio in the range of greater than 1:1 and up to 100:1 Preferably, the Φ:H ratio is greater than 1:1 and up to 10:1.

TABLE 1

Flow Rate Comparison For 3D Bioreactor With Different Aspect Ratios

| # | Ratio (Φ:H) | Diameter (Φ) (cm) | Height (H) (cm) | Flow Rate (μm/sec) |
|---|---|---|---|---|
| 1 | 3:1 | 10.5 | 3.5 | 38.5 |
| 2 | 1:1 | 7.5 | 7.5 | 75.4 |
| 3 | 1:3 | 5 | 15 | 169.8 |

Figure 7B:
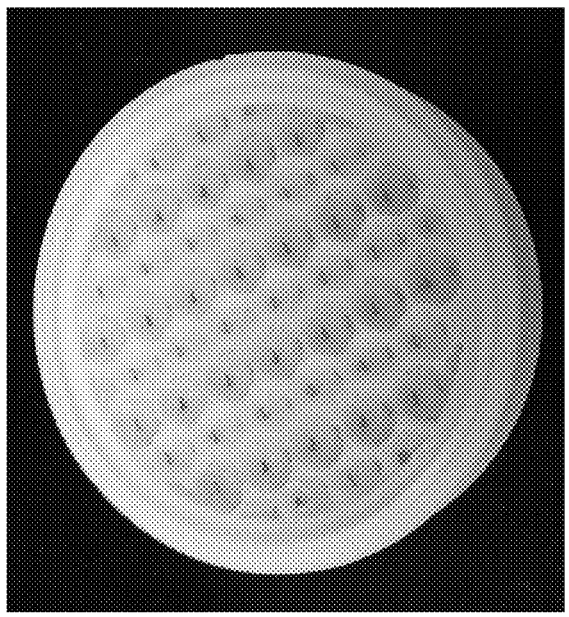
FIG. 7b illustrates the 3D bioreactor fixed-bed together with a bioreactor chamber.
Figure 7D:
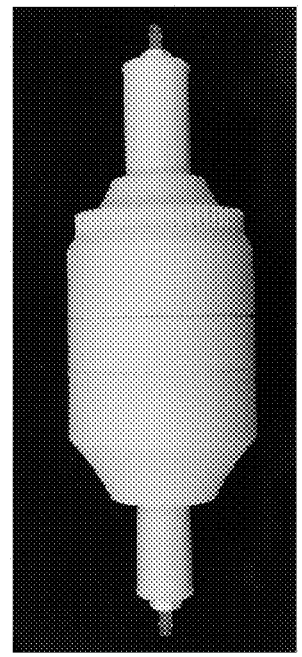
FIG. 7d illustrates an assembled 3D bioreactor.
Figure 7A:
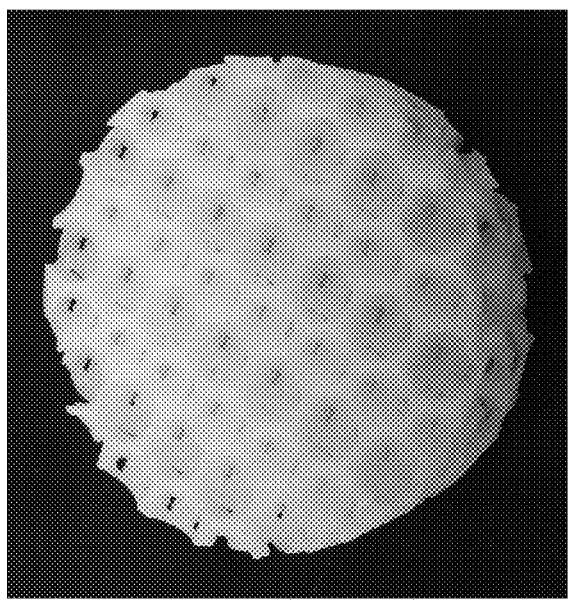
FIG. 7a illustrates a 3D bioreactor fixed-bed generated by FDM 3D printing.
Figure 8:
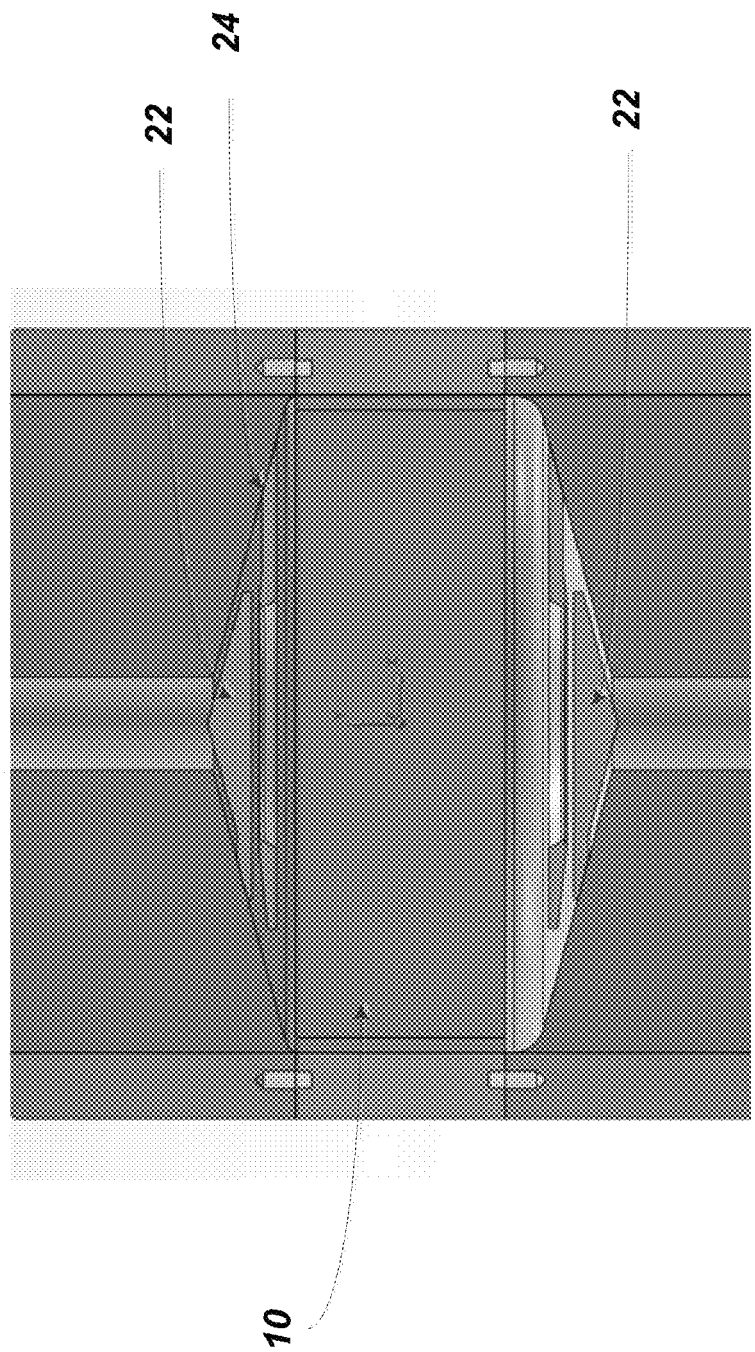
FIG. 8 illustrates two fluid distributors placed at the inlet and outlet of the 3D bioreactor to approach a laminar flow.

FIG. 7a illustrates a 3D bioreactor fixed-bed part generated by FDM 3D printing with interconnected 6 mm diameter voids and 1 mm interconnected pores. This 3D bioreactor was printed with ABS filament. The diameter (Φ) and height (H) of this particular 3D bioreactor is 4.28 cm and 1.43 cm respectively. Accordingly the Φ:H ratio is 3:1. There are about 134 interconnected open-voids included in the fixed-bed. The total interconnected continuous spherical surface area $SA_u$ for cell culturing is about 152 cm². The inlet and outlet wall and fluid distributor 22 at the inlet and outlet (FIG. 8) provides an additional 88 cm² surface area for cell culturing. In other words, there is about 240 cm² total useful surface area in the 3D bioreactor for cell attachment. The fluid distributor can improve the laminar flow through the bioreactor. The fluid distributor is optional if the Reynolds number is <2100 or in the range of greater than 0 up to and not including 2100.

Figure 7C:
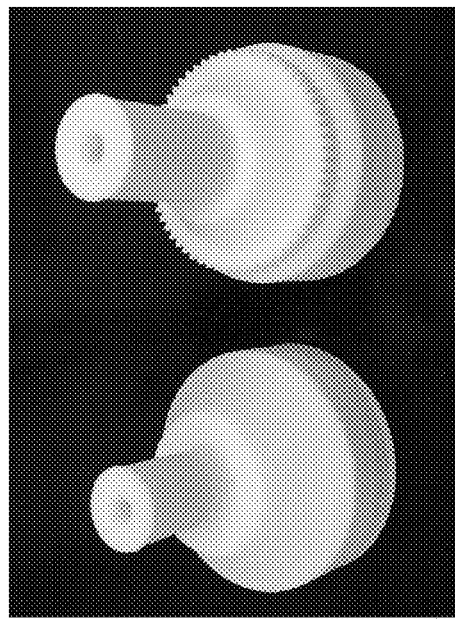
FIG. 7c illustrates the inlet and outlet of a 3D bioreactor.
Figure 7F:
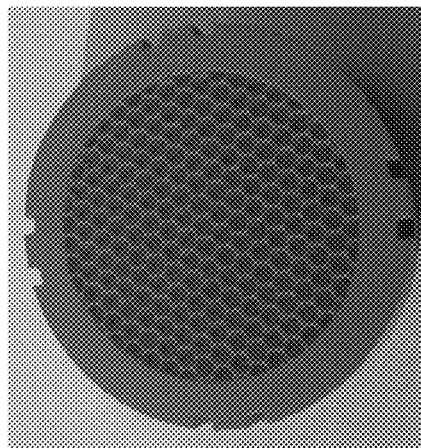
FIG. 7f illustrates a 3D bioreactor fixed bed generated by DLP 3D printing.
Figure 7E:
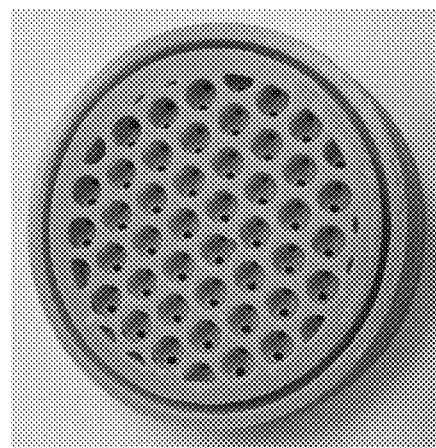
FIG. 7e illustrates a 3D bioreactor fixed-bed generated by SLA 3D printing.

FIG. 7b shows that the fixed-bed of the 3D bioreactor was solvent bound into a bioreactor chamber. This will seal the gaps between the fixed-bed and the chamber wall, which will force the perfusion cell culture medium to pass through the interconnected pores instead of through those gaps. Preferably, the fixed-bed and chamber is printed together as an integrated part to increase the manufacturing efficiency. FIG. 7c illustrates the inlet and outlet of the bioreactor. They are designed geometrically to promote a laminar flow through the fixed-bed. The inlet of the bioreactor optionally contains a built-in rotation gear, which may be coupled to a stepper motor to control the rotation of the bioreactor for uniform cell seeding (see below). The integrated bioreactor is shown in FIG. 7d and is able to connect to ⅛ inch tubing to conduct the fluid flow. Alternatively, the inlet and outlet can be made for repeated usage, where only the inside bioreactor fixed bed is disposable. Also shown in FIG. 7e is a 3D bioreactor fixed bed produced by SLA 3D printing having a 6.0 mm void and a 1.0 mm pore. FIG. 7f is a 3D bioreactor fixed bed using DLP 3D printing having a 3.0 mm void and a 0.5 mm pore.

Figure 9:
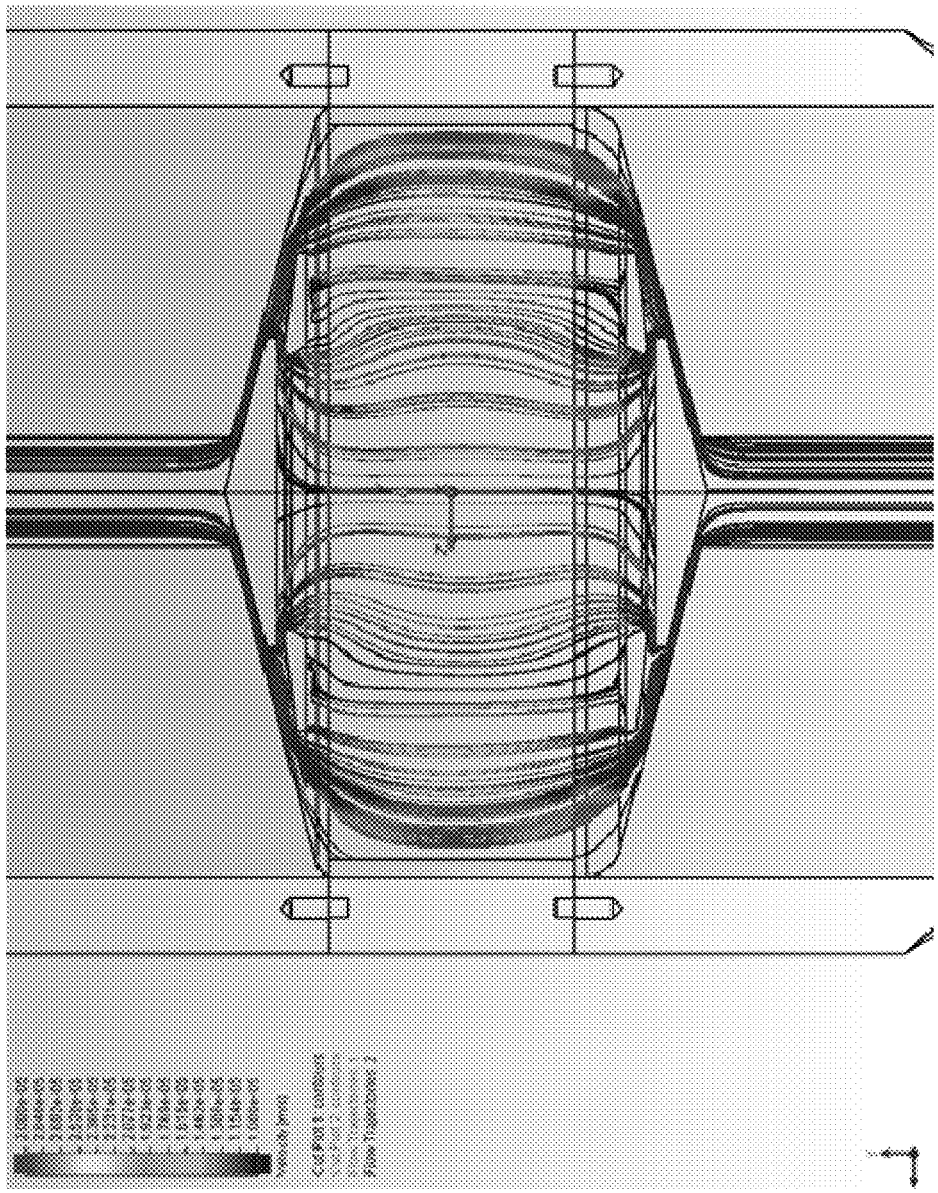
FIG. 9 illustrates a flow rate profile through the 3D bioreactor when using the fluid distributor.

It should next be noted that the fluid distributor 22 (FIG. 8) is preferably such that it will improve the flow uniformity through the 3D bioreactor. The design of the inlet, outlet, and fluid distributor also preferably takes into consideration the following: (1) improve the flow uniformity through the 3D bioreactor; (2) minimization of the dead-volume 24 at inlet and outlet to reduce the overall priming volume of the bioreactor; and (3) preventing bubble collection inside the bioreactor. FIG. 9 shows the flow velocity profile throughout the 3D bioreactor based on CFD simulation by using the fluid distributor. The use of the fluid distributor (FIG. 8) improved the uniformity of the flow. The maximum flow rate (around 30 μm/s) and the minimum flow rate (around 10 μm/s) are relatively close to each other and serve to promote uniform laminar flow (i.e. flow of fluid in relatively parallel layers). A relatively uniform flow rate everywhere in the bioreactor will also provide smaller differences of shear stress to cells residing at different locations in the bioreactor.

The 3D bioreactor can be fabricated by other additive manufacturing technologies such as selective laser sintering (SLS), stereolithography (SLA), Digital Light Processing (DLP), and etc. FIGS. 7b, 7e, 7f.

Figure 10B:
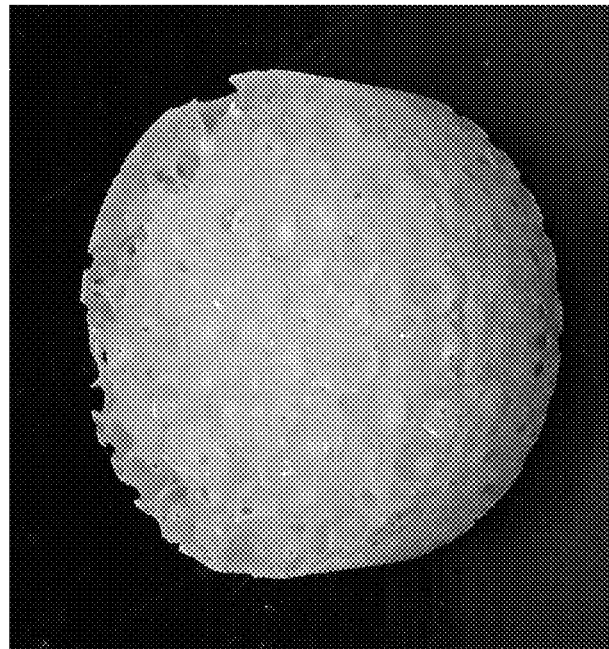
FIGS. 10a and 10b illustrate the formation of a 3D bioreactor by the alternative porogen-leaching method.
Figure 10A:
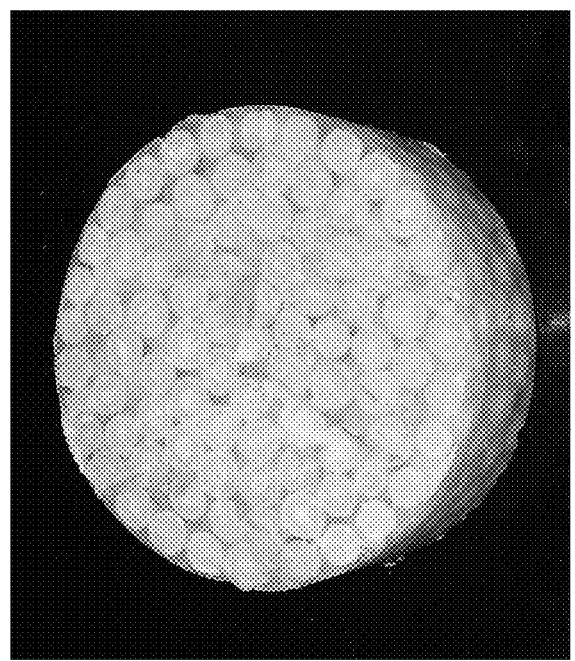

In addition to preparing the 3D bioreactor herein via additive manufacturing or 3D printing, it is contemplated that the 3D bioreactor may be prepared by the traditional porogen-leaching method to provide an interconnected cell culture surface. FIGS. 10a and 10b shows a 3D bioreactor utilizing a porogen-leaching methodology. This is reference to combining porogen and polymer in a mold, followed by leaching out of the porogen to generate pores. The 3D bioreactor in FIG. 10a starts with the step of tightly packing 4.0 mm water-soluble spherical sugar beads (as porogen) in a cylindrical stainless mold by shaking, tapping, and pressing the beads, so that the beads are in contact. The gaps between the beads are filled with acetone containing 5.0% by weight deionized water. This is followed by evaporation the acetone and water under vacuum chamber overnight. The gaps between the beads are then filled with a low viscous polymerizable vinyl monomer such as styrene together with polymerization initiators such as benzoyl or tert-butylperoxybenzoate. The styrene monomer will then polymerize to form polystyrene. The sample remained at 90° C. for 8-12 hours, and then was heated to 115° C. for an additional 3 hours and removed from the oven to provide what is illustrated in FIG. 10a. The sugar beads were then leached out while submerged in an ultrasound water bath to leave the polystyrene 3D bioreactor fixed-bed with interconnected voids. See FIG. 10b. The 3D bioreactor is then extracted with methanol for three days to remove any residual styrene monomer. However, the porogen leaching method not only has a complex manufacturing process, but also is difficult to achieve exact reproducible structures since the packing of porogen beads is a random process.

For the 3D printed bioreactor (FIG. 7d) using ABS, the hydrophobic internal surfaces of the bioreactor is preferably modified to allow for cell adherence. Polydopamine as a primer coating followed with fibronectin coating was therefore utilized to improve the ABS surfaces. To optimize the coating procedure, coating using different concentrations of dopamine hydrochloride (Sigma #H8502) and fibronectin (Sigma #F1141) was evaluated on the substrates of both medical grade and non-medical grade ABS, respectively. Incubation of the ABS surface in a 0.25 mg/mL dopamine dissolved in 10 mM Tris buffer (pH=8.5 at 25° C.) for a period of about 18 hours, resulted in an effective polydopamine layer for the subsequent fibronectin coating. After the polydopamine coating, a four-hour incubation of the ABS surface in fibronectin (Fibronectin from bovine plasma), with the concentration of 50 or 100 μg/mL, promoted mesenchymal stem cell attachment. It should be noted that the use of the polydopamine plus the fibronectin coating is contemplated for use on bioreactors other than the ABS based 3D bioreactor disclosed herein, and in particular on bioreactors that are fabricated with hydrophobic materials. It should also be noted, that the polydopamine primer coating can be combined with other coatings such as peptides, collagen, laminin, multiple cell extracellular matrix proteins, or selected antibodies that are required by particular cell types. After polydopamine is deposited on the bioreactor surface, it can then bind with functional ligands via Michael addition and/or Schiff base reactions. The ligand molecules therefore include nucleophilic functional groups, such as amine and thiol functional groups.

Figure 11C:
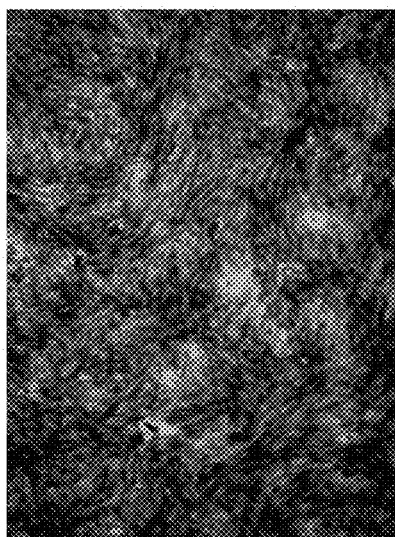
FIGS. 11a, 11b and 11c show cell attachment on a substrate made of non-medical grade ABS resin with polydopamine and fibronectin coating.
Figure 11F:
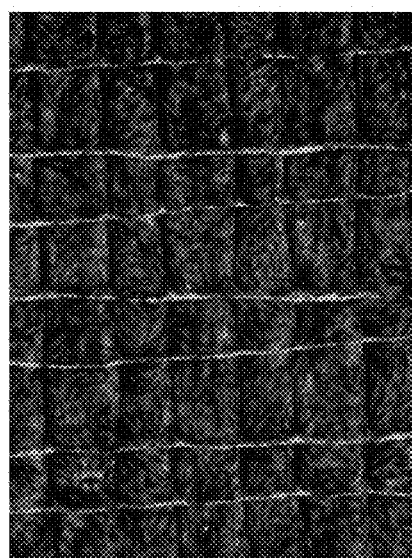
FIGS. 11d, 11e and 11f show cell attachment on a substrate made of medical grade ABS resin with polydopamine and fibronectin coating.
Figure 11B:
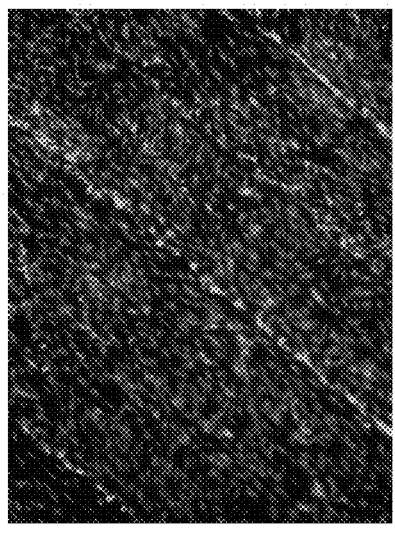
Figure 11E:
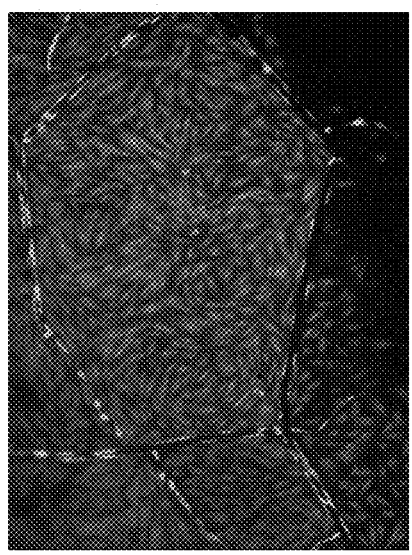
Figure 11A:
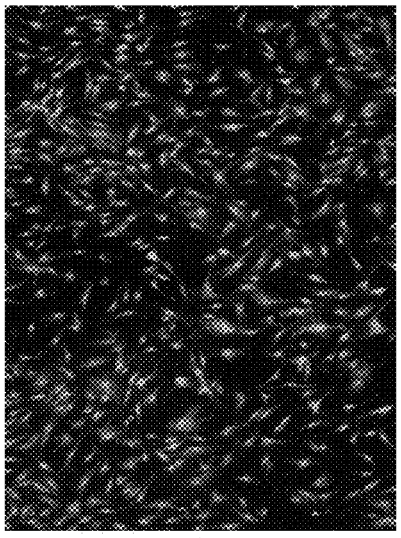
Figure 11D:
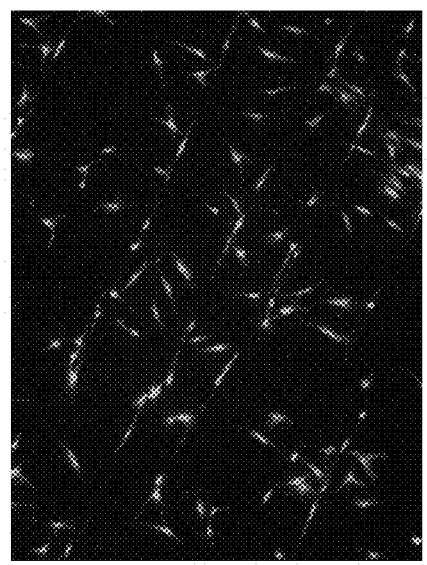

FIGS. 11a, 11b and 11c show cell (labeled with green fluorescence) attachment on non-medical grade ABS at concentrations for coating at 20 μg/ml fibronectin, 50 μg/ml fibronectin and 100 μg/ml fibronectin, respectively, after the polydopamine coating described above. FIGS. 11d, 11e, and 11f show cell attachment on the medical grade ABS at concentrations for coating of 20 μg/ml fibronectin, 50 μg/ml fibronectin and 100 μg/ml fibronectin, respectively. These figures suggest that both medical and non-medical grade ABS have similar performance in cell attachment after polydopamine/fibronectin coating. The coating of fibronectin at 50 μg/ml or 100 μg/ml concentration are preferred for a good cell attachment. These figures also show that cells were aligned to the surface texture that was generated during the 3D printing process. Therefore, a bioreactor surface generated by SLA or DLP 3D printing is preferred for cell expansion.

Figure 12B:
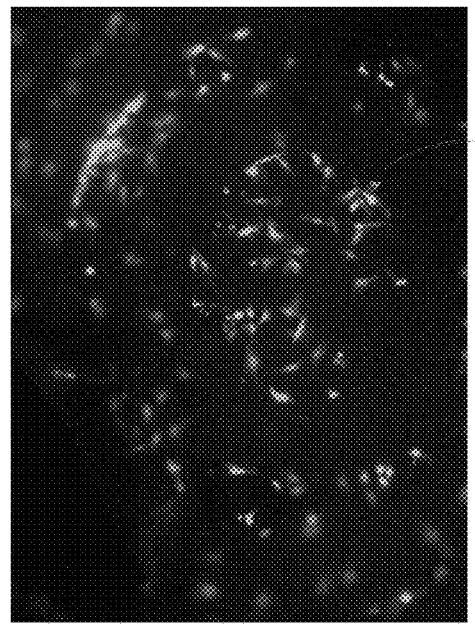
FIGS. 12a, 12b and 12c illustrate cell attachment onto the 3D bioreactor surface.
Figure 12C:
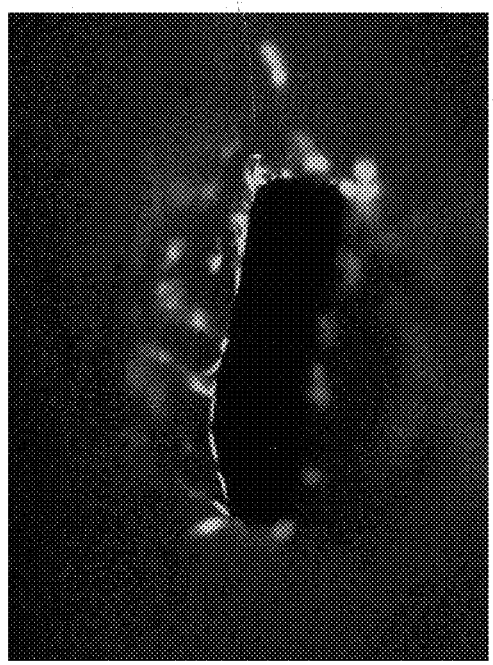
Figure 12A:
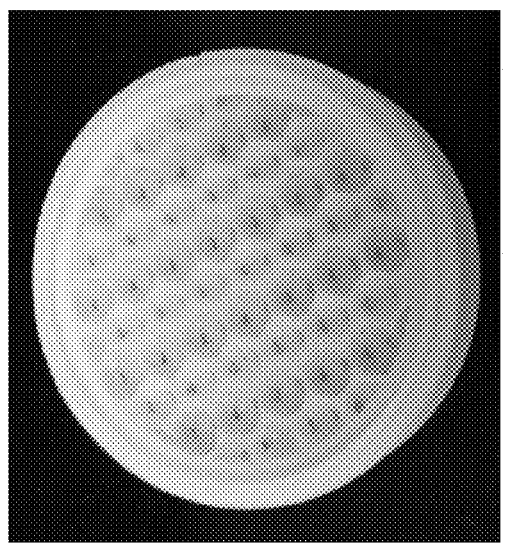

Cell attachment was also evaluated on the 3D bioreactor. Reference is made to FIGS. 12a, 12b and 12c, which illustrate that the cells (labeled with green fluorescence) attach well onto the 3D bioreactor surface. FIG. 12a shows the 3D bioreactor fixed-bed, FIG. 12b shows cells (labeled an arrow pointing to the green fluorescence) seeded on the surface of the spherical voids and FIG. 12c shows cells reside near an interconnected pore between the spherical voids.

As alluded to above (FIG. 3) the 3D bioreactor herein is preferably utilized in a perfusion system. More specifically, a 3D bioreactor fixture was placed inside a 37° C. incubator to maintain the system at body temperature. A Cole-Parmer Masterflex pump was used to deliver cell culture medium to the bioreactor after passing through an oxygenator. A MCQ 3-channel gas blender mixed proper amounts of oxygen, carbon dioxide, and nitrogen to provide a gas mixture feeding to the oxygenator to condition the cell culture medium. With the gas blender, the gas mixture can be controlled to produce a hypoxic condition with around 2% oxygen concentration if needed, which is contemplated to provide relatively more rapid growth of mesenchymal stem cells than at oxygen concentrations of 21%. A gas blender can also adjust the oxygen concentration accordingly with the increase of total cell numbers in the bioreactor. In addition, in the perfusion system, the 3D bioreactor during cell seeding can be preferably positioned horizontally and connected to a stepper motor so that the bioreactor rotates around the bioreactor axis so that the cells are more uniformly seeded inside the bioreactor.

Cell seeding of the 3D bioreactor may be achieved as an example as follows. For the 3D bioreactor illustrated in FIGS. 7a-7d, the total priming volume of the bioreactor is about 22 mL, which includes the volume of the fixed-bed (~16 mL) as well as the space of inlet and outlet (~6 mL). A total of $1.5 \times 10^6$ mesenchymal stem cells, suspended in 25 mL, were infused into the bioreactor. The infusion was carried out by a syringe pump using an infusion rate of 2 mL/min. Right after medium infusion, the bioreactor was placed horizontally on the bioreactor fixture to allow the bioreactor to slowly rotate around its axis with a rotation rate of 0.15 RPM. The bioreactors herein may therefore be rotated at a rotation rate in the range of 0.5 RPM to 0.5 RPM. The bioreactor was allowed to rotate for about 6 hours followed by start of the perfusion flow. A high loading efficiency of 96.3% was measured using this cell loading method.

Figure 13A:
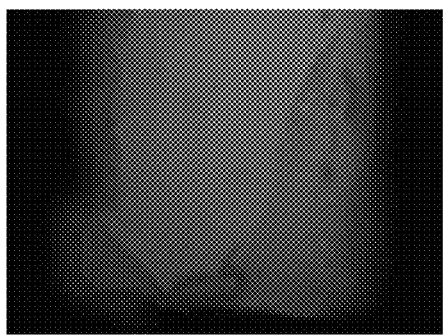
FIGS. 13a, 13c, 13e and 13g illustrate cell attachment on the inlet, fixed-bed, wall and fluid distributor of a 3D bioreactor after cell seeding.
Figure 13B:
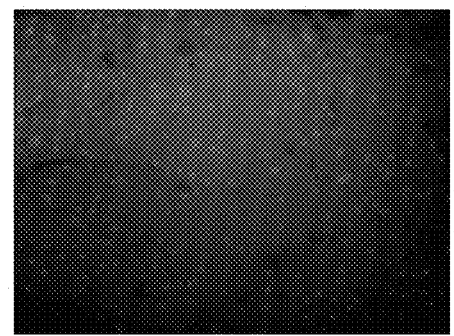
FIGS. 13b, 13d, 13f and 13h illustrate cell distribution after a 7-day culture period.
Figure 13C:
Figure 13D:
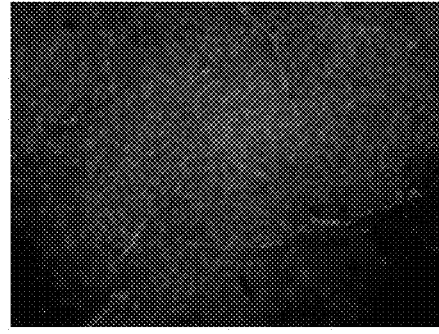
Figure 13E:
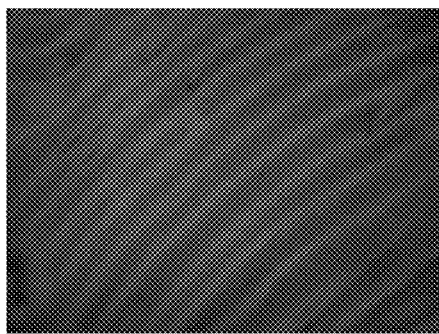
Figure 13F:
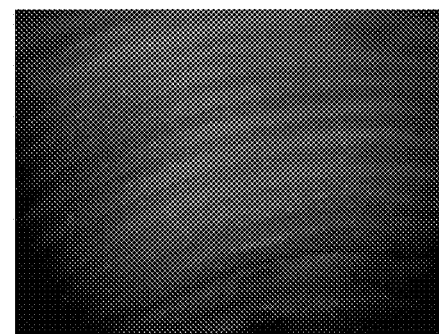
Figure 13G:
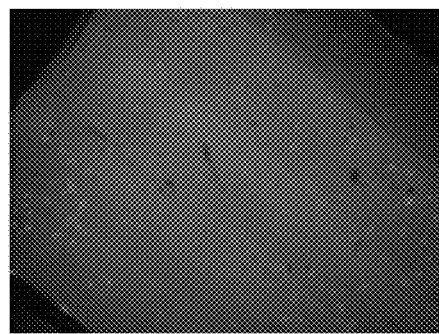
Figure 13H:
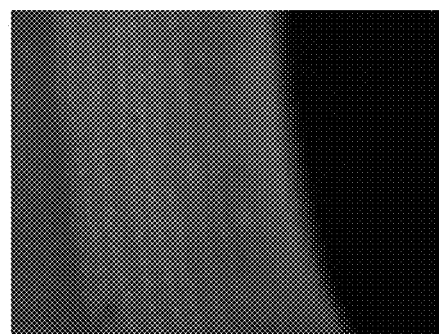

To observe the cell distribution inside bioreactor after seeding, the cells were fixed on the surface of the bioreactor. The fixed cells were then stained with DAPI fluorescence dye (blue) to label the cell nuclear. Then the bioreactor was spliced to open the internal chamber and fluorescence microscopy was used to view the cell attachment and distribution on different surfaces inside the bioreactor. FIGS. 13a, 13c, 13e, and 13g illustrate the cell distribution on the inlet, fixed-bed, wall, and fluid distributor, respectively. All areas indicated seeded cells with a relatively low cell density. The images indicate that the cell seeding was relatively uniformly distributed throughout the bioreactor. FIGS. 13b, 13d, 13f, and 13h indicate the cell distribution on the corresponding surfaces inside the bioreactor after a 7-day expansion period. FIGS. 13a and 13b are the 3D bioreactor inlet wall, FIGS. 13c and 13d are on the 3D bioreactor inner wall, FIGS. 13e and 13f are on the 3D bioreactor center-void spherical surface, and FIGS. 13g and 13h are on the 3D bioreactor flow guider surface.

After a static (no medium perfusion) cell seeding period, the 3D bioreactor is preferably placed in vertical position (the bioreactor inlet is lower than the outlet) during perfusion to prevent the collection of air bubbles inside the bioreactor. The assembled bioreactor shown in FIG. 7d was perfused at the flow rate of 2 mL/min. According to the CFD simulation, the laminar flow rate of 38.5 µm/sec will not generate relatively high shear stress to cells. For this bioreactor shown in FIG. 7 with the fixed-bed diameter of 4.28 cm, or about 14.4 cm² of cross-sectional area the calculated equivalent flow rate is 3.3 mL/min. It should be noted volume perfusion rate depends on the total volume and the cross-sectional area of the bioreactor, the spherical voids diameter and pore diameters inside the bioreactors, as well as cell types, oxygen and nutrition consumption, shear tolerance, etc. Therefore, an optimized perfusion rate will need to be determined via cell manufacturing process development.

The cell culture medium circulated through an oxygenator before flowing into the 3D bioreactor. A gas blender produced a gas mixture containing 74% of $N_2$, 21% of $O_2$, and 5% $CO_2$, which was fed into the oxygenator to refresh the cell culture medium before delivery to the cells inside the bioreactor.

Figure 14:
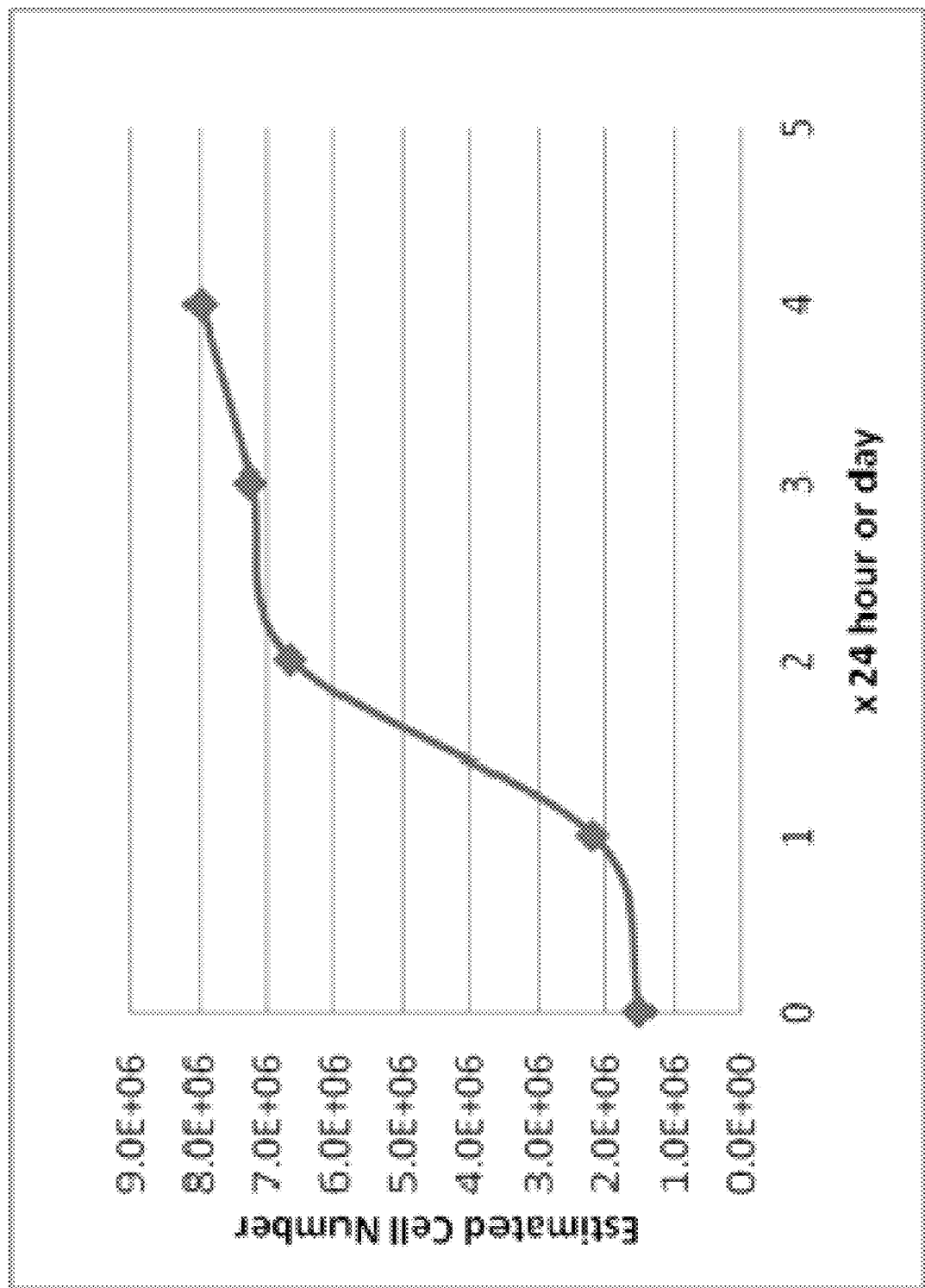
FIG. 14 illustrates the change in cell numbers in the 3D bioreactor over a four-day period.

Every 24-hour, the change in glucose and lactate was measured. Based on glucose and lactate change, the number of cells inside the bioreactor was estimated. FIG. 14 illustrates the change of cell number in the bioreactor over a four-day period. The growth curve shows the three periods of cell growth: that is, slow cell growth (day 1), exponential cell growth (day 2), and growth plateau (days 3 and 4). Around $8 \times 10^6$ cells at harvest are expected after 4-day expansion.

Figure 15:
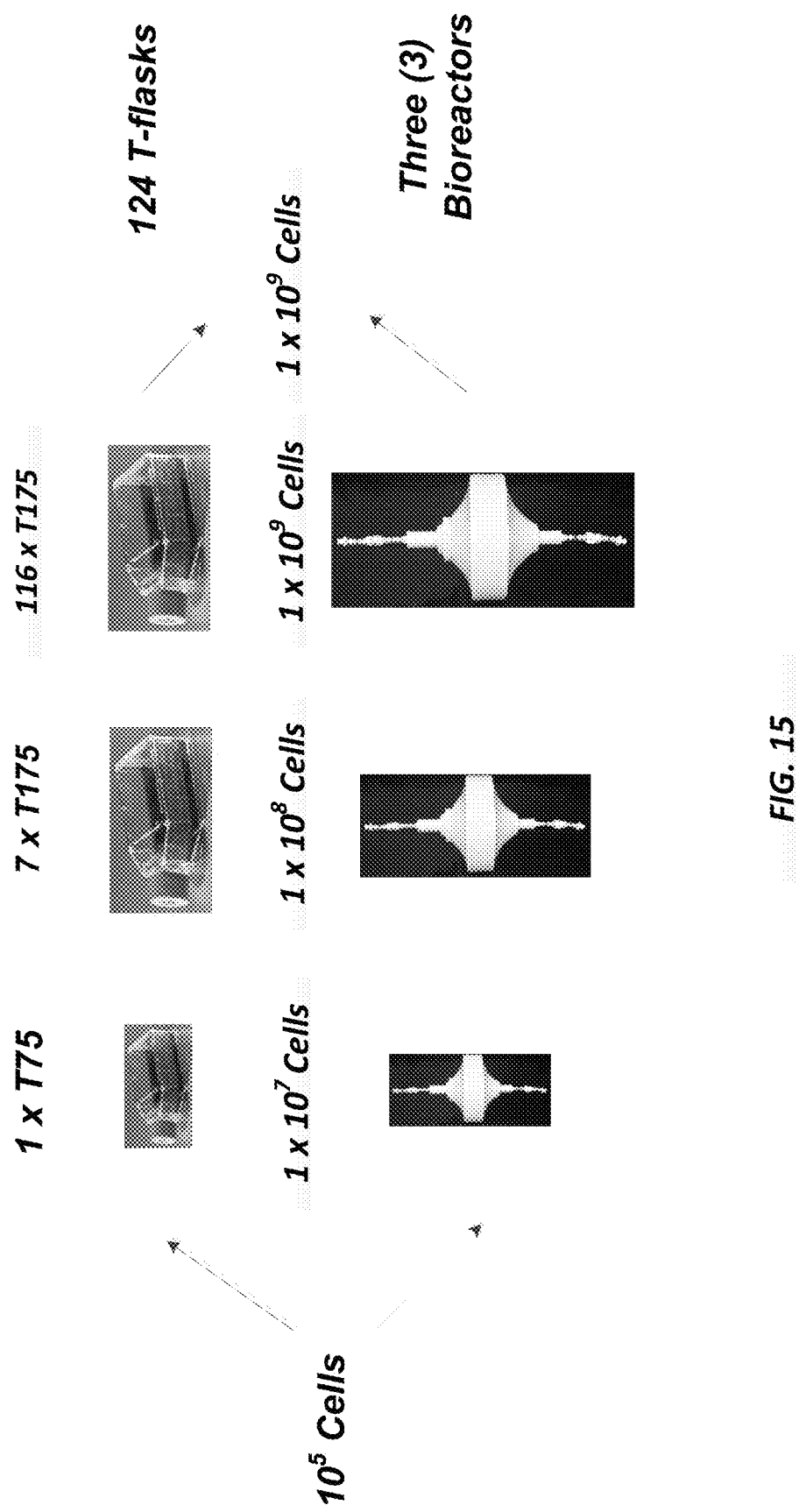
FIG. 15 illustrates a comparison of the use of the 3D bioreactor herein, of three different sizes, versus the use of over 120 T-flasks, to provide the indicated level of cell expansion.

Assuming cells are harvested at 80% of confluence or about $0.4 \times 10^5$ cells/cm², the bioreactors that have the $10^7$, $10^8$, and $10^9$ cell expansion capacity as shown in FIG. 15 would require a total cell culture surface area of 250 cm², 2,500 cm², and 25,000 cm², respectively. Assume the bioreactor is comprised of 2.0 mm diameter spherical voids and twelve (12) 0.5 mm diameter interconnected pores. Each spherical void has SAu=10.16 mm². In other words, the bioreactor that has a $10^7$, $10^8$, and $10^9$ cell expansion capacity requires 2,461, 24,606, and 246,063 of 2.0 mm spherical voids. Considering each spherical void has the volume of 4.19 mm³, a reasonable packing efficiency of 73.6% (according to SolidWorks™ computer simulation), the bioreactor that has a $10^7$, $10^8$, and $10^9$ cell expansion capacity requires a volume of 14.0 cm³, 140.1 cm³, and 1400.8 cm³, respectively. Packing efficiency is reference to the volume occupied by the spherical voids ($V_{occupied}$) divided by the total volume of a 3D cylinder space ($V_{cylinder}$) having a given diameter Φ and height H. For the 3D bioreactor herein, packing efficiency preferably has a value of greater than 64.0%, more preferably greater than 70.0% and most preferably a value greater than 75.0%. Assume the bioreactor's diameter Φ and height H have the ratio of 3:1, then the bioreactors with the $10^7$, $10^8$, and $10^9$ cell expansion capacities shown in FIG. 15 have Φ and H of 5.2 cm (Φ) and 1.7 cm (H), 16.4 cm (Φ) and 5.5 cm (H), 51.8 cm (Φ) and 17.3 cm (H), respectively. The bioreactor is also expected to be scalable to $10^{10}$, $10^{11}$, $10^{12}$ cell expansion capacity.

Cell detachment from the 3D bioreactor was then evaluated. Two reagents were tested for cell detachment. One was the traditional Trypsin-EDTA (0.25%), the other was the new TrypLE Select. The later is expected to be a superior replacement for Trypsin. Using Trypsin with about 5-minute of warm (37° C.) incubation period, it was possible to successfully detach >95% of cells from the 3D bioreactor.

It should now be appreciated from all of the above that one of the additional features of the 3D bioreactor disclosed herein is that one may now design a 3D bioreactor, with particular geometric and void volume requirements, and corresponding available surface area requirements, and be able to achieve (i.e., during fabrication or manufacturing) such targets with relatively minimal variation. For example, one may now identify a design requirement for a 3D bioreactor wherein the one or more internal voids are to have a targeted void volume "$V_t$", and the 3D bioreactor itself is to have a targeted overall surface area for cell culturing "$SA_t$". Accordingly, one may now form such 3D bioreactor wherein the one or more internal voids have an actual void volume "$V_a$" that is within +/−10.0% of $V_t$, or more preferably, +/−5.0% of $V_t$. Similarly, the actual surface area for cell culturing $SA_a$ is within +/−10.0% of $SA_t$, or more preferably +/−5.0% of $SA_t$. Moreover, one may also identify for the internal surface within the targeted voids a targeted geometry for fabrication such as a targeted radius of curvature "$Rc_t$" and then in fabrication the actual radius of curvature "$Rc_a$" of the void internal surface can now be achieved that is within +/−5% of $Rc_t$.

This invention therefore describes a scalable 3D bioreactor which can reduce from using hundreds of T-flasks to only 3 individual 3D bioreactors of different size for the expansion from $10^5$ to $10^9$ cells. As illustrated in FIG. 15, in order to expand $10^5$ cells to $10^9$ cells, one must utilize 124 T-flasks. By contrast, using three of the 3D bioreactors herein of increasing size, one can more readily achieve this level of cell expansion. In addition, the 3D bioreactor facilitates automatic close-loop cell expansion, which will significantly increase the efficiency in cell expansion and meet the cGMP (current Good Manufacturing Practice) regulatory requirements to expand cells for clinical applications. Furthermore, the use of the 3D bioreactor herein will significantly reduce the use of cell culture mediums. The 3D bioreactor herein is one that scalable with a defined geometry, surface coating, and fluidic dynamics to maintain a monolayer cell culture and reduce or prevent cell aggregation (cell-cell contacting and/or stacking), phenotype change, or extracellular production, and is particularly suitable for the expansion of stem cells, primary cells, and other adherent cells, or non-adherent cells under appropriate surface coating of the bioreactor.

What is claimed is:

1. A 3D bioreactor for growth of cells comprising:
   a biocompatible polymeric material having a plurality of voids and a surface area for cell expansion, said plurality of voids having a diameter D in the range of 0.4 mm to 50.0 mm, a plurality of pore openings between said voids having a diameter d in the range of 0.2 mm to 10.0 mm and said voids have a radius of curvature Rc of 5.0 $mm^{-1}$ or less, such that D>d wherein: (a) 90% or more of said voids have a selected void volume (V) that does not vary by more than +/−10.0%; and (b) 90% or more of said pore openings between said voids have a value of d that does not vary by more than +/−10.0%.

2. The 3D bioreactor of claim 1 wherein said voids have a diameter (D) of 0.4 mm to 25.0 mm.

3. The 3D bioreactor of claim 1 wherein said voids have a diameter (D) in the range of 2.0 mm to 10.0 mm.

4. The 3D bioreactor of claim 1 wherein said pores have a diameter (d) in the range of 0.2 mm to 2.0 mm.

5. The 3D bioreactor of claim 1 wherein 95.0% or more of said voids indicate a void volume (V) that does not vary by more than +/−10.0%.

6. The 3D bioreactor of claim 1 wherein 99.0% to 100% of said voids indicate a void volume (V) that does not vary by more than +/−10.0%.

7. The 3D bioreactor of claim 1 wherein 95.0% or more of said pore openings between said voids have a value of d that does not vary by more than +/−10.0%.

8. The 3D bioreactor of claim 1 wherein 99.0 to 100% or more of said pore openings between said voids have a value of d that does not vary by more than +/−10.0%.

9. The 3D bioreactor of claim 1 wherein at least 90.0% of the voids present have 2 pore openings per void.

10. The 3D bioreactor of claim 1 wherein at least 90.0% of the voids present have 8 to 12 pore openings per void.

11. The 3D bioreactor of claim 1 wherein said voids have an internal concave surface.

12. The 3D reactor of claim 1 wherein said voids comprise spherical voids.

13. The 3D bioreactor of claim 12 wherein said spherical voids have a packing efficiency of greater than 64.0% in a 3D cylindrical space.

14. The 3D bioreactor of claim 1 wherein said 3D bioreactor is formed from a material that has a Tensile Modulus of at least 0.01 GPa.

15. The 3D bioreactor of claim 14 wherein said voids have a radius of curvature Rc that is less than or equal to 1.0 $mm^{-1}$.

16. The 3D bioreactor of claim 1 wherein said 3D bioreactor is formed from a material not susceptible to hydrolysis during cell cultivation such that the amount of hydrolysis does not exceed 5.0% by weight of the material present.

17. The 3D bioreactor of claim 1 wherein said bioreactor has a diameter $\Phi$ and a height H and the ratio $\Phi$:H is in the range of greater than 1:1 to 100:1.

18. The 3D bioreactor of claim 1, wherein said bioreactor surface includes polydopamine that is capable of binding additional layer or layers for cell culturing via functional ligands.

19. The 3D bioreactor of claim 1 wherein said voids have a radius of curvature Rc that is less than or equal to 1.0 $mm^{-1}$.

20. The 3D bioreactor of claim 1 wherein said bioreactor comprises a hexagonal close packed lattice.

21. The 3D bioreactor of claim 1 wherein 90.0% to 100% of the voids have 8-12 pore openings per void.

22. A 3D bioreactor for growth of cells comprising:
   a biocompatible polymeric material having a first and second plurality of voids having a surface area for cell expansion;
   said first plurality of voids having a diameter $D_1$ in the range of 0.4 mm to 50.0 mm, a plurality of pore openings between said first plurality of voids having a diameter $d_1$ in the range of 0.2 mm to 10.0 mm and said voids have a radius of curvature Rc of 5.0 $mm^{-1}$ or less, wherein $D_1>d_1$, where 90% or more of the first plurality of voids have a void volume ($V_1$) with a tolerance that does not vary by more than +/−10.0%;
   said second plurality of voids having a diameter $D_2$, a plurality of pore openings between said second plurality of voids having a diameter $d_2$ wherein $D_2>d_2$, wherein 90% of the second plurality of voids have a void volume ($V_2$) with a tolerance that does not vary by more than +/−10.0%; and
   the values of $V_1$ and $V_2$ are different and outside of said tolerance variations such that $$[V_1 +/- 10.0\%] \neq [V_2 +/- 10.0\%].$$

23. The 3D bioreactor of claim 22 wherein said first plurality of voids have a radius of curvature Rc that is less than or equal to 1.0 $mm^{-1}$.

24. A method of forming a 3D bioreactor for growth of cells comprising a plurality of voids having a surface area for cell expansion wherein said voids have a diameter D in the range of 0.4 mm mm to 50.0 mm and a plurality of pore openings between said voids having a diameter d in the range of 0.2 mm to 10.0 mm and said voids have a radius of curvature Rc of 5.0 $mm^{-1}$ or less:

(a) identifying for said plurality of voids a targeted internal void volume ($V_t$);

(b) identifying for said 3D bioreactor a targeted surface area ($SA_t$);

(c) forming said 3D bioreactor from biocompatible polymeric material with: (1) an actual void volume ($V_a$) for said one or more voids, wherein $V_a$ is within +/−10.0% of $V_t$; and (2) an actual surface area ($SA_a$) wherein $SA_a$ is within +/−10.0% of $SA_t$;

(d) positioning said 3D bioreactor in a perfusion system which delivers a flow of a cell culture medium through the 3D bioreactor for promoting said cell growth.

25. The method of claim 24 wherein said 3D bioreactor is seeded with seeding cells on said actual surface area ($SA_a$).

26. The method of claim 24 further comprising delivering said flow of cell culture medium through said 3D bioreactor and forming a monolayer cell culture wherein said cell culture avoids cell-cell contact inhibition and cell differentiation.

27. The method of claim 24 wherein said voids have a radius of curvature Rc that is less than or equal to $1.0 \text{ mm}^{-1}$.

\* \* \* \* \*